US008430898B2

(12) United States Patent
Wiener et al.

(10) Patent No.: US 8,430,898 B2
(45) Date of Patent: Apr. 30, 2013

(54) ULTRASONIC SURGICAL INSTRUMENTS

(75) Inventors: Eitan T. Wiener, Cincinnati, OH (US);
Foster B. Stulen, Mason, OH (US);
Michael J. Stokes, Cincinnati, OH (US);
Karen K. Isaacs, Burlington, KY (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1257 days.

(21) Appl. No.: 11/888,171

(22) Filed: Jul. 31, 2007

(65) Prior Publication Data

US 2009/0036912 A1   Feb. 5, 2009

(51) Int. Cl.
*A61B 17/32* (2006.01)
(52) U.S. Cl.
USPC .......................................................... 606/169
(58) Field of Classification Search .................. 606/157, 606/159, 167–170; 433/86, 102–103, 118–119, 433/141–144, 166; 604/22
See application file for complete search history.

(56) References Cited

U.S. PATENT DOCUMENTS

| | | |
|---|---|---|
| 2,849,788 A | 9/1958 | Creek |
| 3,015,961 A | 1/1962 | Roney |
| 3,526,219 A | 9/1970 | Balamuth |
| 3,636,943 A | 1/1972 | Balamuth |
| 3,776,238 A | 12/1973 | Peyman et al. |
| 3,805,787 A | 4/1974 | Banko |
| 3,862,630 A | 1/1975 | Balamuth |
| 3,918,442 A | 11/1975 | Nikolaev et al. |
| 3,956,826 A | 5/1976 | Perdreaux, Jr. |
| 4,156,187 A | 5/1979 | Murry et al. |
| 4,200,106 A | 4/1980 | Douvas et al. |
| 4,445,063 A | 4/1984 | Smith |
| 4,491,132 A | 1/1985 | Aikins |
| 4,634,420 A | 1/1987 | Spinosa et al. |
| 4,640,279 A | 2/1987 | Beard |
| 4,708,127 A | 11/1987 | Abdelghani |
| 4,832,683 A | 5/1989 | Idemoto et al. |

(Continued)

FOREIGN PATENT DOCUMENTS

| | | |
|---|---|---|
| EP | 0443256 A1 | 8/1991 |
| EP | 0456470 A1 | 11/1991 |

(Continued)

OTHER PUBLICATIONS

Partial International Search Report for PCT/US2008/071702, Feb. 25, 2009 (2 pages).

(Continued)

*Primary Examiner* — Ryan Severson
*Assistant Examiner* — Ashley Cronin

(57) ABSTRACT

A surgical instrument. The surgical instrument may comprise a transducer and an end effector. The transducer may be configured to provide vibrations along a longitudinal axis at a predetermined frequency and may comprise a piezoelectric stack positioned along the longitudinal axis. The transducer also may comprise a first metallic end mass positioned along the longitudinal axis adjacent a first end of the piezoelectric stack and a second metallic end mass positioned along the longitudinal axis adjacent a second end of the piezoelectric stack. The length of the transducer may be greater than or equal to of one wavelength and less than ½ of one wavelength. The end effector may be coupled to the transducer and may extend along the longitudinal axis. The length of the transducer and the end effector may be a multiple of ½ of one wavelength.

11 Claims, 13 Drawing Sheets

U.S. PATENT DOCUMENTS

| | | | |
|---|---|---|---|
| 4,838,853 A | 6/1989 | Parisi | |
| 4,850,354 A | 7/1989 | McGurk-Burleson et al. | |
| 4,865,159 A | 9/1989 | Jamison | |
| 4,896,009 A | 1/1990 | Pawlowski | |
| 4,981,756 A | 1/1991 | Rhandhawa | |
| 5,026,387 A | 6/1991 | Thomas | |
| 5,112,300 A * | 5/1992 | Ureche | 604/22 |
| 5,123,903 A * | 6/1992 | Quaid et al. | 604/22 |
| 5,162,044 A | 11/1992 | Gahn et al. | |
| 5,167,725 A | 12/1992 | Clark et al. | |
| D332,660 S | 1/1993 | Rawson et al. | |
| 5,176,695 A | 1/1993 | Dulebohn | |
| 5,213,569 A | 5/1993 | Davis | |
| 5,221,282 A * | 6/1993 | Wuchinich | 606/99 |
| 5,226,910 A | 7/1993 | Kajiyama et al. | |
| 5,241,236 A | 8/1993 | Sasaki et al. | |
| 5,257,988 A | 11/1993 | L'Esperance, Jr. | |
| 5,261,922 A | 11/1993 | Hood | |
| 5,263,957 A | 11/1993 | Davison | |
| 5,282,800 A | 2/1994 | Foshee et al. | |
| D347,474 S | 5/1994 | Olson | |
| 5,322,055 A | 6/1994 | Davison et al. | |
| 5,324,299 A | 6/1994 | Davison et al. | |
| 5,346,502 A | 9/1994 | Estabrook et al. | |
| 5,366,466 A | 11/1994 | Christian et al. | |
| D354,564 S | 1/1995 | Medema | |
| 5,411,481 A | 5/1995 | Allen et al. | |
| 5,419,761 A | 5/1995 | Narayanan et al. | |
| 5,449,370 A | 9/1995 | Vaitekunas | |
| 5,486,162 A | 1/1996 | Brumbach | |
| 5,500,216 A | 3/1996 | Julian et al. | |
| 5,501,654 A | 3/1996 | Failla et al. | |
| 5,505,693 A | 4/1996 | Mackool | |
| 5,562,609 A | 10/1996 | Brumbach | |
| 5,562,610 A | 10/1996 | Brumbach | |
| 5,601,601 A | 2/1997 | Tal et al. | |
| 5,607,436 A | 3/1997 | Pratt et al. | |
| 5,618,492 A | 4/1997 | Auten et al. | |
| 5,628,760 A | 5/1997 | Knoepfler | |
| 5,630,420 A | 5/1997 | Vaitekunas | |
| D381,077 S | 7/1997 | Hunt | |
| 5,669,922 A | 9/1997 | Hood | |
| 5,674,235 A | 10/1997 | Parisi | |
| 5,690,269 A | 11/1997 | Bolanos et al. | |
| 5,694,936 A | 12/1997 | Fujimoto et al. | |
| 5,713,896 A | 2/1998 | Nardella | |
| 5,741,226 A | 4/1998 | Strukel et al. | |
| 5,810,859 A | 9/1998 | DiMatteo et al. | |
| 5,827,323 A | 10/1998 | Klieman et al. | |
| 5,828,160 A | 10/1998 | Sugishita | |
| 5,843,109 A | 12/1998 | Mehta et al. | |
| 5,879,364 A | 3/1999 | Bromfield et al. | |
| 5,893,835 A | 4/1999 | Witt et al. | |
| 5,897,569 A | 4/1999 | Kellogg et al. | |
| 5,935,143 A | 8/1999 | Hood | |
| 5,935,144 A | 8/1999 | Estabrook | |
| 5,938,633 A | 8/1999 | Beaupre | |
| 5,944,718 A | 8/1999 | Austin et al. | |
| 5,944,737 A | 8/1999 | Tsonton et al. | |
| 5,954,736 A | 9/1999 | Bishop et al. | |
| 5,954,746 A | 9/1999 | Holthaus et al. | |
| 5,957,943 A | 9/1999 | Vaitekunas | |
| 5,968,007 A | 10/1999 | Simon et al. | |
| 5,968,060 A | 10/1999 | Kellogg | |
| D416,089 S | 11/1999 | Barton et al. | |
| 5,989,274 A | 11/1999 | Davison et al. | |
| 5,989,275 A | 11/1999 | Estabrook et al. | |
| 6,033,375 A | 3/2000 | Brumbach | |
| 6,063,098 A | 5/2000 | Houser et al. | |
| 6,066,132 A | 5/2000 | Chen et al. | |
| 6,068,647 A | 5/2000 | Witt et al. | |
| 6,077,285 A | 6/2000 | Boukhny | |
| 6,083,191 A | 7/2000 | Rose | |
| 6,086,584 A | 7/2000 | Miller | |
| 6,090,120 A | 7/2000 | Wright et al. | |
| 6,109,500 A | 8/2000 | Alli et al. | |
| 6,113,594 A | 9/2000 | Savage | |
| 6,139,320 A | 10/2000 | Hahn | |
| 6,152,902 A | 11/2000 | Christian et al. | |
| 6,159,160 A | 12/2000 | Hsei et al. | |
| 6,159,175 A | 12/2000 | Strukel et al. | |
| 6,206,844 B1 | 3/2001 | Reichel et al. | |
| 6,210,403 B1 | 4/2001 | Klicek | |
| 6,214,023 B1 | 4/2001 | Whipple et al. | |
| 6,238,366 B1 | 5/2001 | Savage et al. | |
| D444,365 S | 7/2001 | Bass et al. | |
| 6,254,623 B1 | 7/2001 | Haibel, Jr. et al. | |
| 6,258,034 B1 | 7/2001 | Hanafy | |
| 6,267,761 B1 | 7/2001 | Ryan | |
| 6,273,852 B1 | 8/2001 | Lehe et al. | |
| 6,274,963 B1 | 8/2001 | Estabrook et al. | |
| 6,277,115 B1 | 8/2001 | Saadat | |
| 6,278,218 B1 | 8/2001 | Madan et al. | |
| 6,283,981 B1 | 9/2001 | Beaupre | |
| 6,309,400 B2 | 10/2001 | Beaupre | |
| 6,319,221 B1 | 11/2001 | Savage et al. | |
| 6,325,811 B1 | 12/2001 | Messerly | |
| 6,328,751 B1 | 12/2001 | Beaupre | |
| 6,352,532 B1 | 3/2002 | Kramer et al. | |
| 6,383,194 B1 | 5/2002 | Pothula | |
| 6,387,109 B1 | 5/2002 | Davison et al. | |
| 6,391,042 B1 | 5/2002 | Cimino | |
| 6,416,486 B1 | 7/2002 | Wampler | |
| 6,423,073 B2 | 7/2002 | Bowman | |
| 6,423,082 B1 | 7/2002 | Houser et al. | |
| 6,432,118 B1 | 8/2002 | Messerly | |
| 6,436,114 B1 | 8/2002 | Novak et al. | |
| 6,436,115 B1 | 8/2002 | Beaupre | |
| 6,443,969 B1 | 9/2002 | Novak et al. | |
| 6,454,781 B1 | 9/2002 | Witt et al. | |
| 6,454,782 B1 | 9/2002 | Schwemberger | |
| 6,458,142 B1 | 10/2002 | Faller et al. | |
| 6,480,796 B2 | 11/2002 | Wiener | |
| 6,485,490 B2 | 11/2002 | Wampler et al. | |
| 6,491,708 B2 | 12/2002 | Madan et al. | |
| 6,497,715 B2 | 12/2002 | Satou | |
| 6,500,188 B2 | 12/2002 | Harper et al. | |
| 6,524,316 B1 | 2/2003 | Nicholson et al. | |
| 6,537,291 B2 | 3/2003 | Friedman et al. | |
| 6,543,456 B1 | 4/2003 | Freeman | |
| 6,544,260 B1 | 4/2003 | Markel et al. | |
| 6,561,983 B2 | 5/2003 | Cronin et al. | |
| 6,582,451 B1 | 6/2003 | Marucci et al. | |
| 6,589,200 B1 | 7/2003 | Schwemberger et al. | |
| 6,589,239 B2 | 7/2003 | Khandkar et al. | |
| 6,623,501 B2 | 9/2003 | Heller et al. | |
| 6,626,926 B2 | 9/2003 | Friedman et al. | |
| 6,633,234 B2 | 10/2003 | Wiener et al. | |
| 6,662,127 B2 | 12/2003 | Wiener et al. | |
| 6,663,941 B2 | 12/2003 | Brown et al. | |
| 6,676,660 B2 | 1/2004 | Wampler et al. | |
| 6,678,621 B2 | 1/2004 | Wiener et al. | |
| 6,679,899 B2 | 1/2004 | Wiener et al. | |
| 6,682,544 B2 | 1/2004 | Mastri et al. | |
| 6,716,215 B1 | 4/2004 | David et al. | |
| 6,733,506 B1 | 5/2004 | McDevitt et al. | |
| 6,773,444 B2 | 8/2004 | Messerly | |
| 6,786,383 B2 | 9/2004 | Stegelmann | |
| 6,790,216 B1 | 9/2004 | Ishikawa | |
| 6,869,439 B2 | 3/2005 | White et al. | |
| 6,875,220 B2 | 4/2005 | Du et al. | |
| 6,908,472 B2 | 6/2005 | Wiener et al. | |
| 6,929,632 B2 | 8/2005 | Nita et al. | |
| D509,589 S | 9/2005 | Wells | |
| 6,945,981 B2 | 9/2005 | Donofrio et al. | |
| D511,145 S | 11/2005 | Donofrio et al. | |
| 6,976,969 B2 | 12/2005 | Messerly | |
| 6,977,495 B2 | 12/2005 | Donofrio | |
| 6,984,220 B2 | 1/2006 | Wuchinich | |
| 7,041,088 B2 | 5/2006 | Nawrocki et al. | |
| 7,074,219 B2 | 7/2006 | Levine et al. | |
| 7,077,039 B2 | 7/2006 | Gass et al. | |
| 7,077,853 B2 | 7/2006 | Kramer et al. | |
| 7,108,695 B2 | 9/2006 | Witt et al. | |
| 7,118,564 B2 | 10/2006 | Ritchie et al. | |
| 7,135,018 B2 | 11/2006 | Ryan et al. | |
| 7,135,030 B2 | 11/2006 | Schwemberger et al. | |

| | | |
|---|---|---|
| 7,153,315 B2 | 12/2006 | Miller |
| 7,156,189 B1 | 1/2007 | Bar-Cohen et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,163,548 B2 | 1/2007 | Stulen et al. |
| 7,179,271 B2 | 2/2007 | Friedman et al. |
| 7,204,820 B2 | 4/2007 | Akahoshi |
| 7,223,229 B2 | 5/2007 | Inman et al. |
| 7,229,455 B2 | 6/2007 | Sakurai et al. |
| 7,273,483 B2 | 9/2007 | Wiener et al. |
| 7,331,410 B2 | 2/2008 | Yong et al. |
| 7,380,695 B2 | 6/2008 | Doll et al. |
| 7,390,317 B2 | 6/2008 | Taylor et al. |
| D576,725 S | 9/2008 | Shumer et al. |
| D578,643 S | 10/2008 | Shumer et al. |
| D578,644 S | 10/2008 | Shumer et al. |
| D578,645 S | 10/2008 | Shumer et al. |
| 7,431,704 B2 | 10/2008 | Babaev |
| 7,472,815 B2 | 1/2009 | Shelton, IV et al. |
| 7,479,148 B2 | 1/2009 | Beaupre |
| 7,479,160 B2 | 1/2009 | Branch et al. |
| 7,503,893 B2 | 3/2009 | Kucklick |
| D594,983 S | 6/2009 | Price et al. |
| 2001/0025184 A1 | 9/2001 | Messerly |
| 2001/0039419 A1 | 11/2001 | Francischelli et al. |
| 2002/0019649 A1 | 2/2002 | Sikora et al. |
| 2002/0077550 A1 | 6/2002 | Rabiner et al. |
| 2002/0156493 A1 | 10/2002 | Houser et al. |
| 2003/0055443 A1 | 3/2003 | Spotnitz |
| 2003/0204199 A1 | 10/2003 | Novak et al. |
| 2003/0212332 A1 | 11/2003 | Fenton et al. |
| 2004/0030254 A1 | 2/2004 | Babaev |
| 2004/0047485 A1 | 3/2004 | Sherrit et al. |
| 2004/0092921 A1 | 5/2004 | Kadziauskas et al. |
| 2004/0097919 A1 | 5/2004 | Wellman et al. |
| 2004/0097996 A1 | 5/2004 | Rabiner et al. |
| 2004/0199193 A1 | 10/2004 | Hayashi et al. |
| 2004/0204728 A1 | 10/2004 | Haefner |
| 2004/0260300 A1 | 12/2004 | Gorensek et al. |
| 2005/0049546 A1 | 3/2005 | Messerly et al. |
| 2005/0143769 A1 | 6/2005 | White et al. |
| 2005/0165345 A1 | 7/2005 | Laufer et al. |
| 2005/0177184 A1 | 8/2005 | Easley |
| 2005/0192610 A1 | 9/2005 | Houser et al. |
| 2005/0209620 A1 | 9/2005 | Du et al. |
| 2005/0261581 A1 | 11/2005 | Hughes et al. |
| 2005/0261588 A1 | 11/2005 | Makin et al. |
| 2005/0288659 A1 | 12/2005 | Kimura et al. |
| 2006/0030797 A1 | 2/2006 | Zhou et al. |
| 2006/0079878 A1 | 4/2006 | Houser |
| 2006/0084963 A1 | 4/2006 | Messerly |
| 2006/0190034 A1 | 8/2006 | Nishizawa et al. |
| 2006/0211943 A1 | 9/2006 | Beaupre |
| 2006/0235306 A1 | 10/2006 | Cotter et al. |
| 2006/0253050 A1 | 11/2006 | Yoshimine et al. |
| 2007/0016235 A1 | 1/2007 | Tanaka et al. |
| 2007/0016236 A1 | 1/2007 | Beaupre |
| 2007/0055228 A1 | 3/2007 | Berg et al. |
| 2007/0060915 A1 | 3/2007 | Kucklick |
| 2007/0131034 A1 | 6/2007 | Ehlert et al. |
| 2007/0149881 A1 | 6/2007 | Rabin |
| 2007/0162050 A1 | 7/2007 | Sartor |
| 2007/0219481 A1 | 9/2007 | Babaev |
| 2007/0249941 A1 | 10/2007 | Salehi et al. |
| 2007/0265560 A1 | 11/2007 | Soltani et al. |
| 2007/0275348 A1 | 11/2007 | Lemon |
| 2007/0282335 A1 | 12/2007 | Young et al. |
| 2007/0287933 A1 | 12/2007 | Phan et al. |
| 2008/0009848 A1 | 1/2008 | Paraschiv et al. |
| 2008/0058585 A1 | 3/2008 | Novak et al. |
| 2008/0058775 A1 | 3/2008 | Darian et al. |
| 2008/0058845 A1 | 3/2008 | Shimizu et al. |
| 2008/0082039 A1 | 4/2008 | Babaev |
| 2008/0177268 A1 | 7/2008 | Daum et al. |
| 2008/0188878 A1 | 8/2008 | Young |
| 2008/0200940 A1 | 8/2008 | Eichmann et al. |
| 2008/0208231 A1 | 8/2008 | Ota et al. |
| 2008/0234708 A1 | 9/2008 | Houser et al. |
| 2008/0234709 A1 | 9/2008 | Houser |
| 2008/0234710 A1 | 9/2008 | Neurohr et al. |
| 2008/0234711 A1 | 9/2008 | Houser et al. |
| 2008/0287948 A1 | 11/2008 | Newton et al. |
| 2009/0030311 A1 | 1/2009 | Stulen et al. |
| 2009/0030351 A1 | 1/2009 | Wiener et al. |
| 2009/0030437 A1 | 1/2009 | Houser et al. |
| 2009/0030438 A1 | 1/2009 | Stulen |
| 2009/0030439 A1 | 1/2009 | Stulen |
| 2009/0036911 A1 | 2/2009 | Stulen |
| 2009/0036913 A1 | 2/2009 | Wiener et al. |
| 2009/0036914 A1 | 2/2009 | Houser |
| 2009/0082716 A1 | 3/2009 | Akahoshi |
| 2009/0105750 A1 | 4/2009 | Price et al. |
| 2009/0143795 A1 | 6/2009 | Robertson |
| 2009/0143796 A1 | 6/2009 | Stulen et al. |
| 2009/0143806 A1 | 6/2009 | Witt et al. |
| 2010/0036405 A1 | 2/2010 | Giordano et al. |

FOREIGN PATENT DOCUMENTS

| | | |
|---|---|---|
| EP | 0482195 B1 | 4/1992 |
| EP | 0612570 B1 | 6/1997 |
| EP | 0908148 B1 | 1/2002 |
| EP | 1199044 B1 | 12/2005 |
| EP | 1844720 A1 | 10/2007 |
| EP | 1862133 A1 | 12/2007 |
| EP | 1974771 A1 | 10/2008 |
| EP | 1832259 B1 | 6/2009 |
| WO | WO 01/54590 A1 | 8/2001 |
| WO | WO 2005/122917 | 12/2005 |
| WO | WO 2006/042210 A2 | 4/2006 |
| WO | WO 2007/047531 A2 | 4/2007 |
| WO | WO 2009/027065 A1 | 3/2009 |

OTHER PUBLICATIONS

International Search Report for PCT/US2008/071702, May 19, 2009 (10 pages).
U.S. Appl. No. 12/469,293, filed May 20, 2009.
U.S. Appl. No. 12/469,308, filed May 20, 2009.
U.S. Appl. No. 12/503,775, filed Jul. 15, 2009.
U.S. Appl. No. 12/503,769, filed Jul. 15, 2009.
U.S. Appl. No. 12/503,770, filed Jul. 15, 2009.
U.S. Appl. No. 12/503,766, filed Jul. 15, 2009.
U.S. Appl. No. 12/490,906, filed Jun. 24, 2009.
U.S. Appl. No. 12/490,922, filed Jun. 24, 2009.
U.S. Appl. No. 12/490,933, filed Jun. 24, 2009.
U.S. Appl. No. 12/490,948, filed Jun. 24, 2009.
Technology Overview, printed from www.harmonicscalpel.com, Internet site, website accessed on Jun. 13, 2007, (3 pages).
Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
AST Products, Inc., "Principles of Video Contact Angle Analysis," 20 pages, (date unknown).
Lim et al., "A Review of Mechanism Used in Laparoscopic Surgical Instruments," Mechanism and Machine Theory, vol. 38, pp. 1133-1147, (2003).
Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).
U.S. Appl. No. 11/998,758, filed Nov. 30, 2007.
U.S. Appl. No. 12/245,158, filed Oct. 3, 2008.
U.S. Appl. No. 29/292,295, filed Oct. 5, 2007.
U.S. Appl. No. 11/998,543, filed Nov. 30, 2007.
U.S. Appl. No. 29/327,737, filed Nov. 12, 2008.
U.S. Appl. No. 12/274,884, filed Nov. 20, 2008.
AST Products, Inc., "Principles of Video Contact Angle Analysis," 20 pages, (2006).
U.S. Appl. No. 12/703,860, filed Feb. 11, 2010.
U.S. Appl. No. 12/703,864, filed Feb. 11, 2010.
U.S. Appl. No. 12/703,866, filed Feb. 11, 2010.
U.S. Appl. No. 12/703,870, filed Feb. 11, 2010.
U.S. Appl. No. 12/703,875, filed Feb. 11, 2010.

U.S. Appl. No. 12/703,877, filed Feb. 11, 2010.
U.S. Appl. No. 12/703,879, filed Feb. 11, 2010.
U.S. Appl. No. 12/703,885, filed Feb. 11, 2010.
U.S. Appl. No. 12/703,893, filed Feb. 11, 2010.
U.S. Appl. No. 12/703,899, filed Feb. 11, 2010.
U.S. Appl. No. 12/732,702, filed Mar. 26, 2010.

* cited by examiner

ULTRASONIC SURGICAL INSTRUMENTS

BACKGROUND

Ultrasonic instruments, including both hollow core and solid core instruments are used for the safe and effective treatment of many medical conditions. Ultrasonic instruments, and particularly solid core ultrasonic instruments, are advantageous because they may be used to cut and/or coagulate tissue using energy in the form of mechanical vibrations transmitted to a surgical end effector at ultrasonic frequencies. Ultrasonic vibrations, when transmitted to organic tissue at suitable energy levels and using a suitable end effector, may be used to cut, dissect or coagulate tissue or to separate muscle tissue off bone. Ultrasonic instruments may be used for open procedures or minimally invasive procedures, such as endoscopic or laparoscopic procedures, wherein the end effector is passed through a trocar to reach the surgical site.

Activating or exciting the single or multiple element end effector (e.g., cutting blade, ball coagulator) of such instruments at ultrasonic frequencies induces longitudinal, transverse or tortional vibratory movement that generates localized heat within adjacent tissue, facilitating both cutting and coagulating. Because of the nature of ultrasonic instruments, a particular ultrasonically actuated end effector may be designed to perform numerous functions, including, for example, cutting and coagulating.

Ultrasonic vibration is induced in the surgical end effector by electrically exciting a transducer, for example. The transducer may be constructed of one or more piezoelectric or magnetostrictive elements in the instrument hand piece. Vibrations generated by the transducer section are transmitted to the surgical end effector via an ultrasonic waveguide extending from the transducer section to the surgical end effector. The waveguides and end effectors may be designed to resonate at the same frequency as the transducer. Therefore, when an end effector is attached to a transducer the overall system frequency is the same frequency as the transducer itself The transducer and the end effector may be designed to resonate at two different frequencies and when joined or coupled may resonate at a third frequency. The zero-to-peak amplitude of the longitudinal ultrasonic vibration at the tip, d, of the end effector behaves as a simple sinusoid at the resonant frequency as given by:

$$d = A \sin(\omega t)$$

where:
$\omega$=the radian frequency which equals $2\pi$ times the cyclic frequency, f; and
A=the zero-to-peak amplitude.
The longitudinal excursion is defined as the peak-to-peak (p-t-p) amplitude, which is just twice the amplitude of the sine wave or 2A.

Ultrasonic surgical instruments may be divided into two types, single element end effector devices and multiple-element end effector devices. Single element end effector devices include instruments such as scalpels (e.g., blades, sharp hook blades, dissecting hook blades, curved blades) and ball coagulators. Single-element end effector instruments have limited ability to apply blade-to-tissue pressure when the tissue is soft and loosely supported. Substantial pressure may be necessary to effectively couple ultrasonic energy to the tissue. This inability to grasp the tissue results in a further inability to fully coapt tissue surfaces while applying ultrasonic energy, leading to less-than-desired hemostasis and tissue joining. In these cases, multiple-element end effectors may be used. Multiple-element end effector devices, such as clamping coagulators, include a mechanism to press tissue against an ultrasonic blade that can overcome these deficiencies.

One drawback of existing ultrasonic instruments is their size. The large size and bulkiness of existing ultrasonic instruments can make it more difficult for clinicians to manipulate the instruments in surgical environments where fine movement is required and can also obstruct the vision of the clinician. This may limit the usefulness of ultrasonic instruments in small surgical sites. Also, because of the bulkiness of existing transducers, many existing ultrasonic instruments position the transducer proximal from the end effector, requiring an extended, and often relatively inflexible wave guide. As a result, articulation of the end effector and blade may be difficult or impossible. This limits the usefulness of existing ultrasonic instruments in endoscopic and laparoscopic surgical environments.

SUMMARY

In one general aspect, the various embodiments are directed to a surgical instrument. The surgical instrument may comprise a transducer and an end effector. The transducer may be configured to provide vibrations along a longitudinal axis at a predetermined frequency and may comprise a piezoelectric stack positioned along the longitudinal axis. The transducer also may comprise a first metallic end mass positioned along the longitudinal axis adjacent a first end of the piezoelectric stack and a second metallic end mass positioned along the longitudinal axis adjacent a second end of the piezoelectric stack. The length of the transducer may be greater than or equal to ¼ of one wavelength and less than ½ of one wavelength. The end effector may be coupled to the transducer and may extend along the longitudinal axis. The length of the transducer and the end effector may be a multiple of ½ of one wavelength.

In another general aspect, the various embodiments are directed to another surgical instrument comprising a transducer and an end effector. The transducer may be configured to provide vibrations along a longitudinal axis at a predetermined frequency. The transducer may comprise a piezoelectric stack positioned along the longitudinal axis, a first metallic end mass positioned along the longitudinal axis adjacent a first end of the piezoelectric stack, and a second metallic end mass positioned along the longitudinal axis adjacent a second end of the piezoelectric stack. The end effector may extend along the longitudinal axis and be coupled to the transducer. According to various embodiments, the amplitude gain of the transducer may be equal to one.

In yet another general aspect, the various embodiments are directed to a surgical instrument. The surgical instrument may comprise a transducer configured to provide vibrations along a longitudinal axis at a predetermined frequency and a housing coupled to the transducer. The transducer may comprise a piezoelectric stack, a first metallic end mass and a second metallic end mass. The piezoelectric stack may be positioned along the longitudinal axis about ¼ of one wavelength from the first end of the transducer. The first and second metallic end masses may be positioned along the longitudinal axis adjacent first and second respective ends of the piezoelectric stack. According to various embodiments, the length of the transducer is equal to about one wavelength. Also, the transducer may define a first mounting point and a second mounting point, where the first mounting point is positioned ¼ of one wavelength from the first end of the transducer along the longitudinal axis, and the second mounting point is positioned ¼ of one wavelength from a second end of the transducer along the longitudinal axis. The housing may be coupled to the transducer at the first and second mounting points.

In an additional general aspect, the various embodiments are directed to a surgical instrument comprising a flexible member, a transducer, and an end effector positioned distally from the transducer. The transducer may be coupled to a distal portion of the flexible member and may be positioned to provide vibrations along a longitudinal axis at a predetermined frequency. The transducer may comprise: a piezoelectric stack positioned along the longitudinal axis, a first metallic end mass and a second metallic end mass. The first and second metallic end masses may be positioned along the longitudinal axis adjacent first and second respective ends of the piezoelectric stack.

In another general aspect, the various embodiments are directed to a surgical instrument comprising a surgical device, a sleeve configured to receive the surgical device and a rail positioned along an interior portion of the sleeve. The surgical device may comprise a feature for receiving the rail and may be slidable along the rail. Also, the surgical device may comprise a transducer positioned to provide vibrations along a longitudinal axis at a predetermined frequency and an end effector positioned distally from the transducer.

In yet another general aspect, the various embodiments are directed to a surgical instrument comprising a first operation member and a second operation member. The first and second operation members may be pivotable towards one another about a pivot point. The surgical instrument also may comprise a transducer positioned along a longitudinal axis of the first operation member to provide vibrations at a predetermined frequency along the longitudinal axis. In addition, the surgical instrument may comprise an end effector coupled to the transducer and extending distally along the longitudinal axis. A clamp pad may be coupled to the second operation member and may move towards the end effector when the first operation member and the second operation member are pivoted towards one another about the pivot point.

FIGURES

The novel features of the various embodiments are set forth with particularity in the appended claims. The various embodiments, however, both as to organization and methods of operation, together with further objects and advantages thereof, may best be understood by reference to the following description, taken in conjunction with the accompanying drawings as follows.

DESCRIPTION

Before explaining the various embodiments in detail, it should be noted that the embodiments are not limited in their application or use to the details of construction and arrangement of parts illustrated in the accompanying drawings and description. The illustrative embodiments may be implemented or incorporated in other embodiments, variations and modifications, and may be practiced or carried out in various ways. For example, the surgical instruments and blade configurations disclosed below are illustrative only and not meant to limit the scope or application thereof. Furthermore, unless otherwise indicated, the terms and expressions employed herein have been chosen for the purpose of describing the illustrative embodiments for the convenience of the reader and are not to limit the scope thereof.

Examples of ultrasonic surgical instruments and blades are disclosed in U.S. Pat. Nos. 5,322,055 and 5,954,736, 6,309, 400 B2, 6,278,218B1, 6,283,981 B1, and 6,325,811 B1, which are incorporated herein by reference in their entirety. These references disclose ultrasonic surgical instrument designs and blade designs where a longitudinal mode of the blade is excited. The result is a longitudinal standing wave within the instrument. Accordingly, the instrument has nodes, where the longitudinal motion is equal to zero, and antinodes, where the longitudinal motion is at its maximum. The instrument's tissue effector is often positioned at an anti-node, maximizing its longitudinal motion.

Various embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments is defined solely by the claims. The features illustrated or described in connection with one exemplary embodiment may be combined with the features of other embodiments. Such modifications and variations are intended to be included within the scope of the claims.

Figure 1:
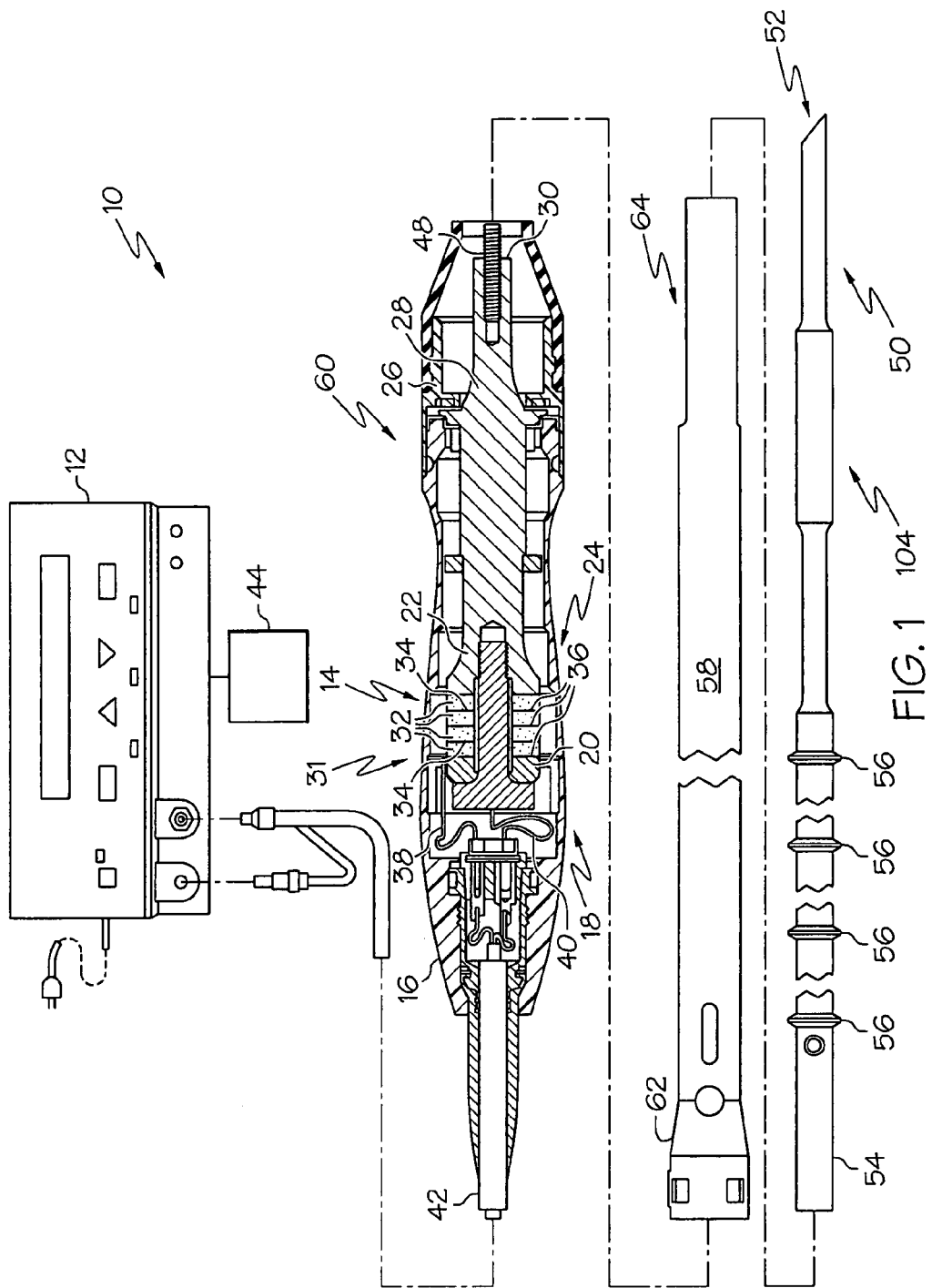
FIG. 1 illustrates one embodiment of an ultrasonic system.

FIG. 1 illustrates one embodiment of an ultrasonic system 10. The ultrasonic system 10 may comprise an ultrasonic signal generator 12 coupled to an ultrasonic transducer 14, a hand piece assembly 60 comprising a hand piece housing 16, and an ultrasonically actuatable single element end effector or ultrasonically actuatable blade 50. The ultrasonic transducer 14, which is known as a "Langevin stack", generally includes a transduction portion 18, a first resonator portion or end-bell 20, and a second resonator portion or fore-bell 22, and ancillary components. The total construction of these portions is a resonator. The ultrasonic transducer 14 is preferably an integral number of one-half system wavelengths (n$\lambda$/2: wherein "n" is any positive integer; e.g., n=1, 2, 3 . . . ) in length as will be described in more detail later. An acoustic assembly 24 includes the ultrasonic transducer 14, a nose cone 26, a velocity transformer 28, and a surface 30.

It will be appreciated that the terms "proximal" and "distal" are used herein with reference to a clinician gripping the hand piece assembly 60. Thus, the end effector 50 is distal with respect to the more proximal hand piece assembly 60. It will be further appreciated that, for convenience and clarity, spatial terms such as "top" and "bottom" also are used herein with respect to the clinician gripping the hand piece assembly 60. However, surgical instruments are used in many orientations and positions, and these terms are not intended to be limiting and absolute.

The distal end of the end-bell 20 is connected to the proximal end of the transduction portion 18, and the proximal end of the fore-bell 22 is connected to the distal end of the transduction portion 18. The fore-bell 22 and the end-bell 20 have a length determined by a number of variables, including the thickness of the transduction portion 18, the density and modulus of elasticity of the material used to manufacture the end-bell 20 and the fore-bell 22, and the resonant frequency of the ultrasonic transducer 14. The fore-bell 22 may be tapered inwardly from its proximal end to its distal end to amplify the ultrasonic vibration amplitude as the velocity transformer 28, or alternately may have no amplification. A suitable vibrational frequency range may be about 20 Hz to 120 kHz and a well-suited vibrational frequency range may be about 30-100 kHz and one example operational vibrational frequency may be approximately 55.5 kHz, for example.

Piezoelectric stack 31 may include one or more piezoelectric elements 32, which may be fabricated from any suitable material, such as, for example, lead zirconate-titanate, lead meta-niobate, lead titanate, barium titanate or other piezoelectric ceramic material. Each of positive electrodes 34, negative electrodes 36, and the piezoelectric elements 32 may have a bore extending through the center. The positive and negative electrodes 34 and 36 are electrically coupled to wires 38 and 40, respectively. The wires 38 and 40 are encased within a cable 42 and electrically connectable to the ultrasonic signal generator 12 of the ultrasonic system 10.

The ultrasonic transducer 14 of the acoustic assembly 24 converts the electrical signal from the ultrasonic signal generator 12 into mechanical energy that results in primarily a standing acoustic wave of longitudinal vibratory motion of the ultrasonic transducer 14 and the end effector 50 at ultrasonic frequencies. In another embodiment, the vibratory motion of the ultrasonic transducer may act in a different direction. For example, the vibratory motion may comprise a local longitudinal component of a more complicated motion of the tip of the ultrasonic system 10. A suitable generator is available as model number GEN01, from Ethicon Endo-Surgery, Inc., Cincinnati, Ohio. When the acoustic assembly 24 is energized, a vibratory motion standing wave is generated through the acoustic assembly 24. The ultrasonic system 10 may be designed to operate at a resonance such that an acoustic standing wave pattern of a predetermined amplitude is produced. The amplitude of the vibratory motion at any point along the acoustic assembly 24 may depend upon the location along the acoustic assembly 24 at which the vibratory motion is measured. A minimum or zero crossing in the vibratory motion standing wave is generally referred to as a node (e.g., where motion is usually minimal), and a local absolute value maximum or peak in the standing wave is generally referred to as an anti-node (e.g., where motion is usually maximal). The distance between an anti-node and its nearest node is one-quarter wavelength ($\lambda$/4).

The wires 38 and 40 transmit an electrical signal from the ultrasonic signal generator 12 to the positive electrodes 34 and the negative electrodes 36. The piezoelectric elements 32 are energized by the electrical signal supplied from the ultrasonic signal generator 12 in response to a switch 44 to produce an acoustic standing wave in the acoustic assembly 24. The switch 44 may be configured to be actuated by a clinician's foot. The electrical signal causes the piezoelectric elements 32 to expand and contract in a continuous manner along the axis of the voltage gradient, producing longitudinal waves of ultrasonic energy. The straining of the elements causes large alternating compressional and tensile forces within the material. These forces in the piezoelectric elements 32 manifest as repeated small displacements resulting in large alternating compression and tension forces within the material. The repeated small displacements cause the piezoelectric elements 32 to expand and contract in a continuous manner along the axis of the voltage gradient, producing longitudinal waves of ultrasonic energy. The ultrasonic energy is transmitted through the acoustic assembly 24 to the end effector 50 via a transmission component or ultrasonic transmission waveguide 104. According to various embodiments, the waveguide 104, end effector 50 and blade 52 may all be referred to generally as the end effector.

In order for the acoustic assembly 24 to deliver energy to the end effector 50, all components of the acoustic assembly 24 must be acoustically coupled to the end effector 50. The distal end of the ultrasonic transducer 14 may be acoustically coupled at the surface 30 to the proximal end of the ultrasonic transmission waveguide 104 by a threaded connection such as a stud 48.

The components of the acoustic assembly 24 are preferably acoustically tuned such that the length of any assembly is an integral number of one-half wavelengths (n$\lambda$/2), where the wavelength $\lambda$ is the wavelength of a pre-selected or operating longitudinal vibration drive frequency $f_d$ of the acoustic assembly 24, and where n is any positive integer. It is also contemplated that the acoustic assembly 24 may incorporate any suitable arrangement of acoustic elements.

The ultrasonic end effector 50 may have a length substantially equal to an integral multiple of one-half system wavelengths ($\lambda/2$). A distal end or blade 52 of the ultrasonic end effector 50 may be disposed near an antinode in order to provide the maximum longitudinal excursion of the distal end. When the transducer assembly is energized, the distal end 52 of the ultrasonic end effector 50 may be configured to move in the range of, for example, approximately 10 to 500 microns peak-to-peak, and preferably in the range of about 30 to 150 microns at a predetermined vibrational frequency.

The ultrasonic end effector 50 may be coupled to the ultrasonic transmission waveguide 104. The ultrasonic end effector 50 and the ultrasonic transmission guide 104 as illustrated are formed as a single unit construction from a material suitable for transmission of ultrasonic energy such as, for example, Ti6Al4V (an alloy of Titanium including Aluminum and Vanadium), Aluminum, Stainless Steel, or other suitable materials. Alternately, the ultrasonic end effector 50 may be separable (and of differing composition) from the ultrasonic transmission waveguide 104, and coupled by, for example, a stud, weld, glue, quick connect, or other suitable known methods. The ultrasonic transmission waveguide 104 may have a length substantially equal to an integral number of one-half system wavelengths ($\lambda/2$), for example. The ultrasonic transmission waveguide 104 may be preferably fabricated from a solid core shaft constructed out of material suitable to propagate ultrasonic energy efficiently, such as the titanium alloy discussed above, (e.g., Ti-6Al-4V) or any suitable aluminum alloy, or other alloys, for example.

The ultrasonic transmission waveguide 104 comprises a longitudinally projecting attachment post 54 at a proximal end to couple to the surface 30 of the ultrasonic transmission waveguide 104 by a threaded connection such as the stud 48. In the embodiment illustrated in FIG. 1, the ultrasonic transmission waveguide 104 comprises a plurality of stabilizing silicone rings or compliant supports 56 positioned at a plurality of nodes. The silicone rings 56 dampen undesirable vibration and isolate the ultrasonic energy from an outer sheath 58 assuring the flow of ultrasonic energy in a longitudinal direction to the distal end 52 of the end effector 50 with maximum efficiency.

As shown in FIG. 1, the outer sheath 58 protects a user of the ultrasonic instrument 10 and a patient from the ultrasonic vibrations of the ultrasonic transmission waveguide 104. The sheath 58 generally includes a hub 62 and an elongated tubular member 64. The tubular member 64 is attached to the hub 62 and has an opening extending longitudinally therethrough. The sheath 58 may be threaded or snapped onto the distal end of the housing 16. The ultrasonic transmission waveguide 104 extends through the opening of the tubular member 64 and the silicone rings 56 isolate the ultrasonic transmission waveguide 104 from the outer sheath 58. The outer sheath 58 may be attached to the waveguide 104 with an isolator pin 112. The hole in the waveguide 104 may occur nominally at a displacement. The waveguide 104 may screw or snap onto the hand piece assembly 60 by the stud 48. The flat portions of the hub 62 may allow the assembly to be torqued to a required level.

The hub 62 of the sheath 58 is preferably constructed from ULTEM®, and the tubular member 64 is fabricated from stainless steel. Alternatively, the ultrasonic transmission waveguide 104 may have polymeric material surrounding it to isolate it from outside contact.

The distal end of the ultrasonic transmission waveguide 104 may be coupled to the proximal end of the end effector 50 by an internal threaded connection, preferably at or near an antinode. It is contemplated that the end effector 50 may be attached to the ultrasonic transmission waveguide 104 by any suitable means, such as a welded joint or the like. Although the end effector 50 may be detachable from the ultrasonic transmission waveguide 104, it is also contemplated that the end effector 50 and the ultrasonic transmission waveguide 104 may be formed as a single unitary piece.

Figure 2:
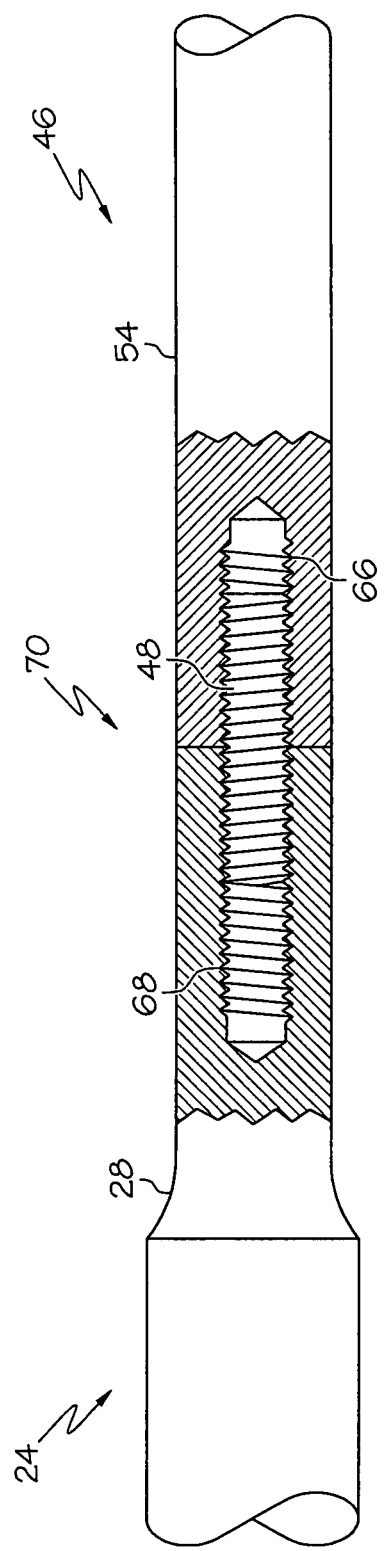
FIG. 2 illustrates one embodiment of a connection union/joint for an ultrasonic instrument.

FIG. 2 illustrates one embodiment of a connection union/joint 70 for an ultrasonic instrument. The connection union/joint 70 may be formed between the attachment post 54 of the ultrasonic transmission waveguide 104 and the surface 30 of the velocity transformer 28 at the distal end of the acoustic assembly 24. The proximal end of the attachment post 54 comprises a female threaded substantially cylindrical recess 66 to receive a portion of the threaded stud 48 therein. The distal end of the velocity transformer 28 also may comprise a female threaded substantially cylindrical recess 68 to receive a portion of the threaded stud 40. The recesses 66, 68 are substantially circumferentially and longitudinally aligned. In another embodiment (not shown), the stud is an integral component of the end of the ultrasonic transducer. For example, the treaded stud and the velocity transformer may be of a single unit construction with the stud projecting from a distal surface of the velocity transformer at the distal end of the acoustic assembly. In this embodiment, the stud is not a separate component and does not require a recess in the end of the transducer.

Figure 3:
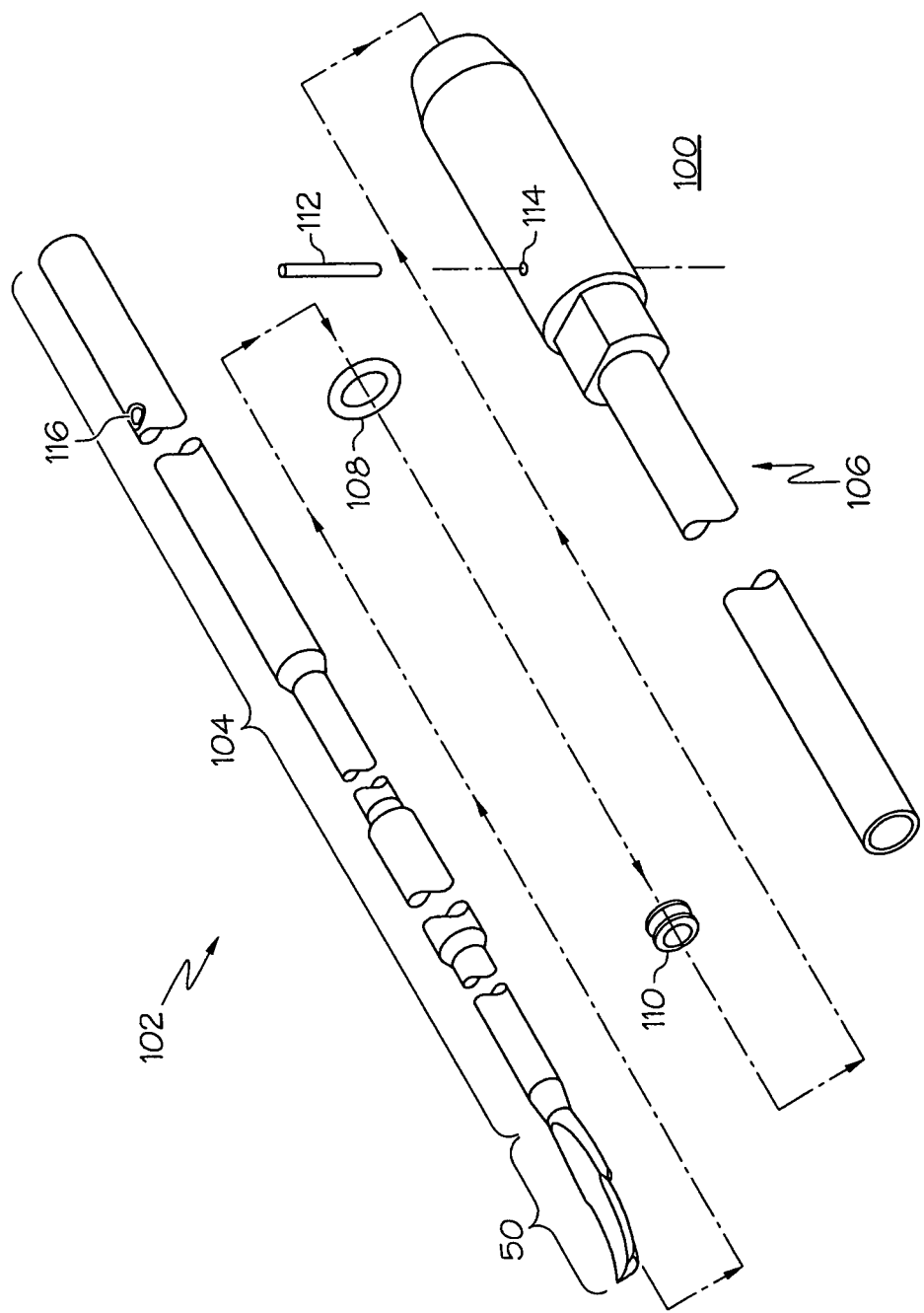
FIG. 3 illustrates an exploded perspective view of one embodiment of a surgical instrument that may be employed with the ultrasonic system shown in FIG. 1.

FIG. 3 illustrates an exploded perspective view of one embodiment of a sterile ultrasonic surgical instrument 100. The ultrasonic surgical instrument 100 may be employed with the above-described ultrasonic system 10. However, as described herein, those of ordinary skill in the art will understand that the various embodiments of the ultrasonic surgical instruments disclosed herein as well as any equivalent structures thereof could conceivably be effectively used in connection with other known ultrasonic surgical instruments without departing from the scope thereof. Thus, the protection afforded to the various ultrasonic surgical blade embodiments disclosed herein should not be limited to use only in connection with the exemplary ultrasonic surgical instrument described above.

The ultrasonic surgical instrument 100 may be sterilized by methods known in the art such as, for example, gamma radiation sterilization, Ethelyne Oxide processes, autoclaving, soaking in sterilization liquid, or other known processes. In the illustrated embodiment, an ultrasonic transmission assembly 102, which may be generally referred to as the end effector, may include the ultrasonic end effector 50 and the ultrasonic transmission waveguide 104. The ultrasonic end effector 50 and the ultrasonic transmission waveguide 104 are illustrated as a single unit construction from a material suitable for transmission of ultrasonic energy such as, for example, Ti6Al4V (an alloy of Titanium including Aluminum and Vanadium), Aluminum, Stainless Steel, or other known materials. Alternately, the ultrasonic end effector 50 may be separable (and of differing composition) from the ultrasonic transmission waveguide 104, and coupled by, for example, a stud, weld, glue, quick connect, or other known methods. The ultrasonic transmission waveguide 104 may have a length substantially equal to an integral number of one-half system wavelengths ($n\lambda/2$), for example. The ultrasonic transmission waveguide 104 may be preferably fabricated from a solid core shaft constructed out of material that propagates ultrasonic energy efficiently, such as titanium alloy (e.g., Ti-6Al-4V) or an aluminum alloy, for example.

In the embodiment illustrated in FIG. 3, the ultrasonic transmission waveguide 104 is positioned in an outer sheath 106 by a mounting O-ring 108 and a sealing ring 110. One or more additional dampers or support members (not shown) also may be included along the ultrasonic transmission waveguide 104. The ultrasonic transmission waveguide 104 is affixed to the outer sheath 106 by a mounting pin 112 that passes through mounting holes 114 in the outer sheath 106 and a mounting slot 116 in the ultrasonic transmission waveguide 104.

Figure 4:
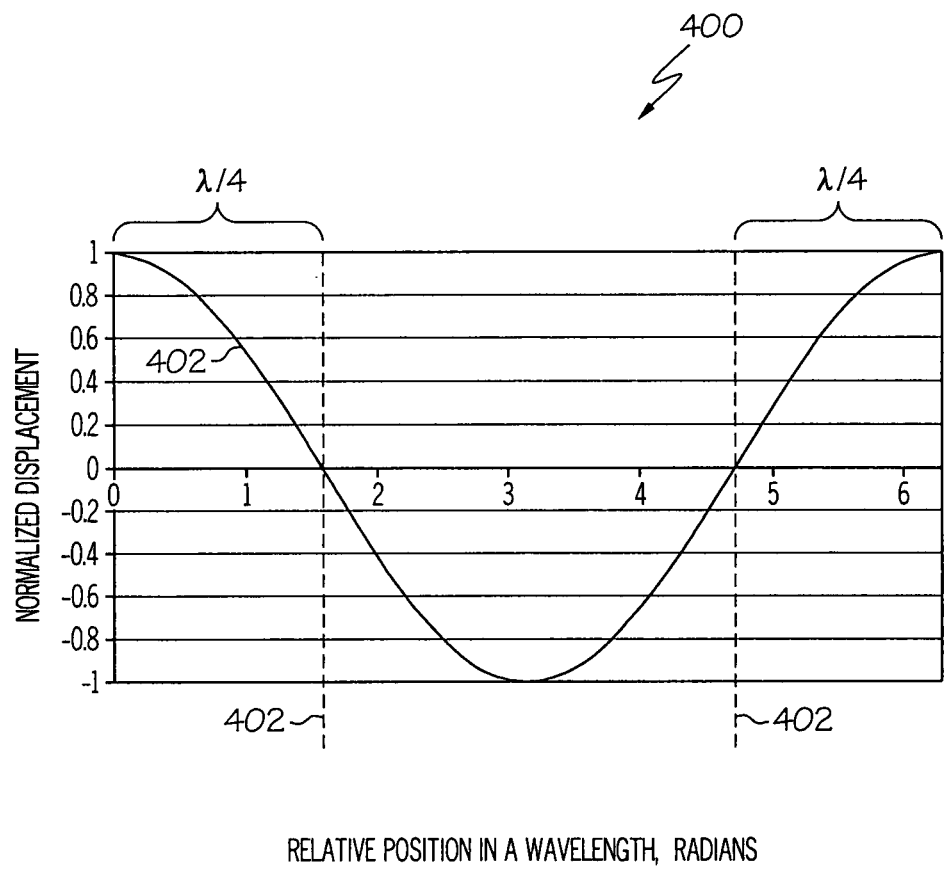
FIG. 4 illustrates one embodiment of a chart showing the displacement of a standing waveform over a full wavelength.

FIG. 4 illustrates one cycle or wavelength of a standing waveform 400 as it would be formed in a full-wavelength transducer. The length of the waveform 400, and thus the length of the transducer, may depend on system frequency and the material from which the transducer is made. For example, in a transducer made of titanium and excited at a frequency of 55.5 kHz, one wavelength may be approximately 3.44 inches. Because it is a full-wavelength, the waveform 400 includes two nodes 402 where the displacement is zero. These are the zero-displacement nodes 402 and they occur at $\lambda/4$ and $3\lambda/4$, or $\lambda/4$ from the respective edges of the waveform 400 on the x-axis. Mounting points for the transducer may be positioned to correspond to the zero-displacement nodes 402.

FIGS. 5-9 illustrate embodiments of full-wavelength ultrasonic transducers that may be used in any suitable ultrasonic system including, for example, the system 10 described above. Because the full-wavelength transducers are longer than typical half-wavelength transducers, they may include a longer piezoelectric stack. For this reason, full-wavelength transducers may be able to deliver power comparable to that of existing larger-diameter half-wavelength transducers. Also, full-wavelength transducers, such as the embodiments shown in FIGS. 5-9 may include multiple mounting points. This may provide increased resistance to prevent the transducers from pivoting within the hand piece housing in response to forces applied at the end effector, and also may provide increased damping to prevent unwanted vibration modes such as transverse and tortional.

Figure 5:
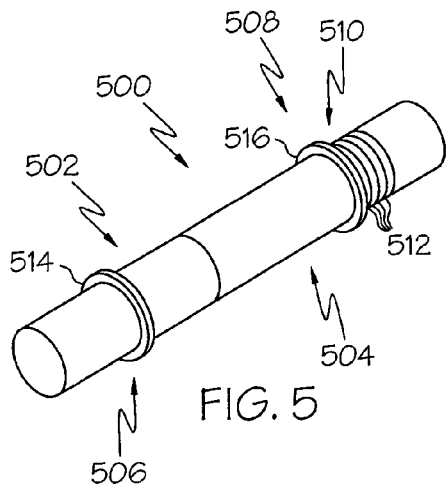
FIG. 5 illustrates one embodiment of a full-wavelength ultrasonic transducer having two mounting points comprising flanges.

FIG. 5 illustrates one embodiment of a full-wavelength ultrasonic transducer 500 having two mounting points 506, 508 comprising flanges 514, 516. The transducer 500 may generally include a piezoelectric stack 510, which may include a series of piezoelectric elements 512. Optionally, the transducer 500 may be divided into an active stage 504, including the piezoelectric stack 510, and a gain stage 502, which may provide amplitude gain. The gain stage 502, for example, may involve a change in the cross-sectional area of the transducer 500 positioned at or near the zero displacement node 402. As described above, the mounting points 514, 516 may be located at the respective zero-displacement nodes in the transducer 500. This may prevent significant amounts of transverse vibration from being transferred from the transducer 500 to the hand piece housing (not shown).

Figure 6:
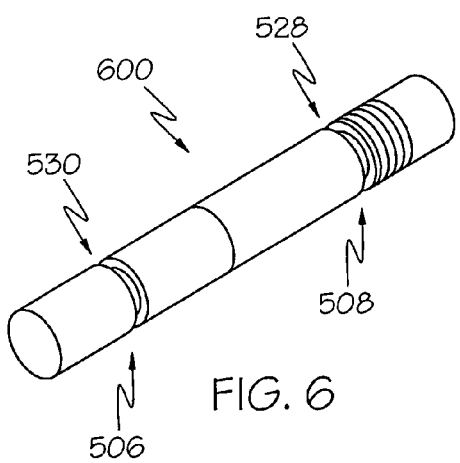
FIG. 6 illustrates one embodiment of a full-wavelength ultrasonic transducer having two mounting points defining grooves.
Figure 7:
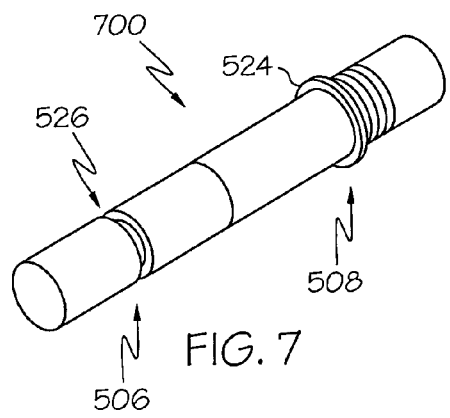
FIGS. 7-8 illustrate embodiments of a full-wavelength ultrasonic transducer having one mounting point comprising a flange and one mounting point defining a groove.
Figure 8:
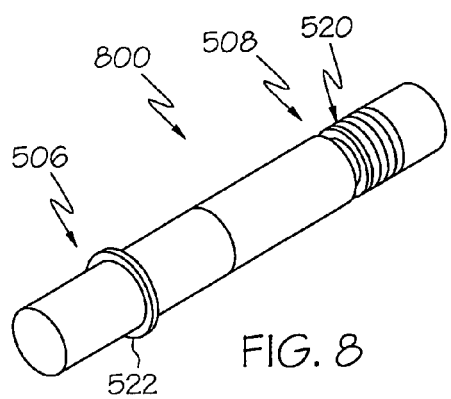
Figure 9:
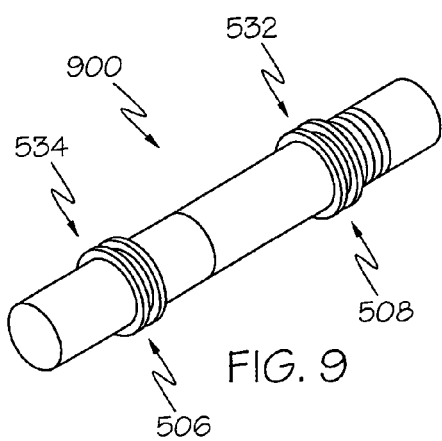
FIG. 9 illustrates one embodiment of a full-wavelength ultrasonic transducer having two mounting points, each comprising a pair of flanges.

The mounting points 506, 508 may take any suitable form. For example, in the embodiment shown in FIG. 5, the mounting points 506, 508 comprise flanges 514, 516 raised above the surface the transducer 500. The hand piece housing, or other frame member, may then include corresponding shapes for receiving the flanges 514, 516. FIG. 6 illustrates one embodiment of a full-wavelength ultrasonic transducer 600 having two mounting points 506, 508 defining grooves 530, 528. The hand piece housing or other frame member (not shown) may include a corresponding feature for coupling with the grooves 530, 528. Also, for example, an O-ring or other type of elastomeric member (not shown) may be positioned within one or both of the groove 530, 528. The O-ring may interface with the hand piece housing or other frame member. FIG. 7 illustrates one embodiment of a full-wavelength ultrasonic transducer 700 having one mounting point 506 defining a groove 526 and one mounting point 508 comprising a flange 524. FIG. 8 illustrates one embodiment of a full-wavelength ultrasonic transducer 800 having one mounting point 506 comprising a flange 522 and one mounting point 508 defining a groove 520. FIG. 9 illustrates one embodiment of a full-wavelength ultrasonic transducer 900 having two mounting points 506, 508. Each of the mounting points 506 508 may comprise a pair of flanges which together define grooves 532, 534. In this way, an O-ring may be held stationary by the flanges without the need for a groove extending into the transducer 500.

Figure 10:
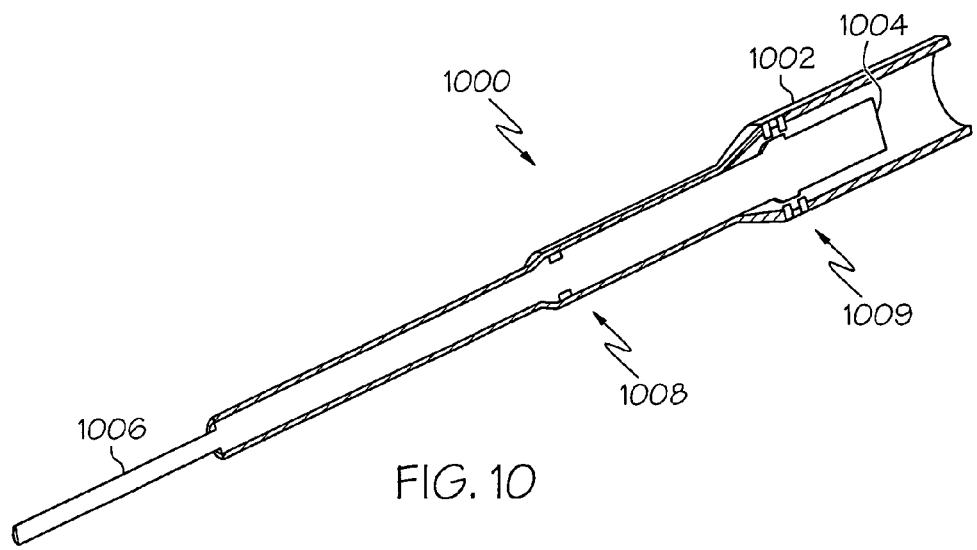
FIG. 10 illustrates one embodiment of a portion of an ultrasonic device including a housing, a transducer and an end effector.

FIG. 10 illustrates an embodiment of a portion 1000 of an ultrasonic device including a housing 1002, a transducer 1004 and an end effector 1006. The transducer 1004 may include mounting points 1008 and 1009 of different dimensions. For example, in the embodiment shown in FIG. 10, the distal mounting point 1008 is shown with a smaller dimension than the proximal mounting point 1009. This may simplify manufacturing by allowing the transducer to be inserted into the housing 1002 from the proximal end.

Figure 11:
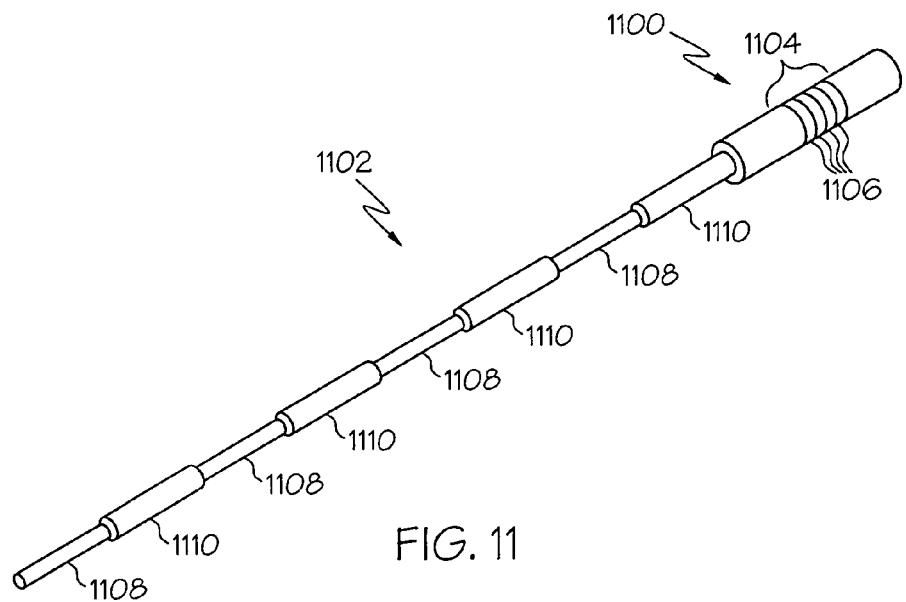
FIG. 11 illustrates one embodiment of a portion of an ultrasonic device including an ultrasonic transducer and end effector.

FIG. 11 illustrates one embodiment of a portion of an ultrasonic device including an ultrasonic transducer 1100 and end effector 1102. The transducer 1100 may include a piezoelectric stack 1104 comprising one or more piezoelectric disks 1106. The transducer 1100 may be constructed as a unity gain or near unity gain transducer. For example, the amplitude of the standing wave at the distal end of the transducer 1100 may be substantially similar to the amplitude of the standing wave at the proximal end of the transducer 1100. In one example embodiment, the amplitude at the distal end of the transducer 1100 may be between 1 and 5 microns peak-to-peak. As described above, it may be desirable for the end effector 1102 to displace at an amplitude of, for example, between 10 and 100 microns peak-to-peak. Accordingly, it may be desirable to configure the end effector 1102 to implement an amplitude gain between its proximal and distal ends. The end effector 1102 is shown with a series of relatively large diameter sections 1110 and relatively small diameter sections 1108. Each transition from a large diameter section 1110 to a small diameter section 1108 may bring about an amplitude gain when the transition occurs near a zero-displacement node. According to various embodiments, the total amplitude gain of the transducer 1100 and end effector 1102 may be between about 10 and 50. For example, the total amplitude gain may be about 40.

Figure 12:
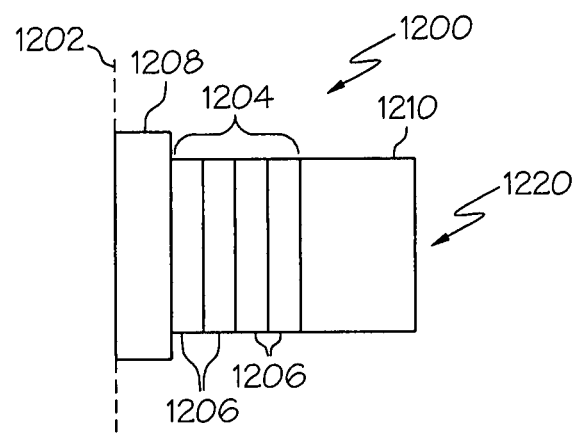
FIG. 12 illustrates one embodiment of a quarter-wavelength ultrasonic transducer.
Figure 13:
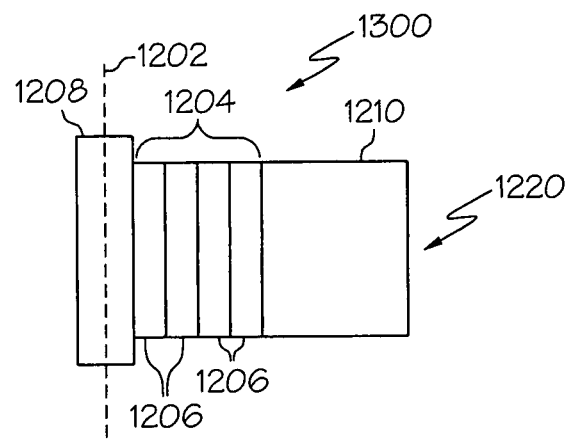
FIG. 13 illustrates one embodiment of an ultrasonic transducer.
Figure 14:
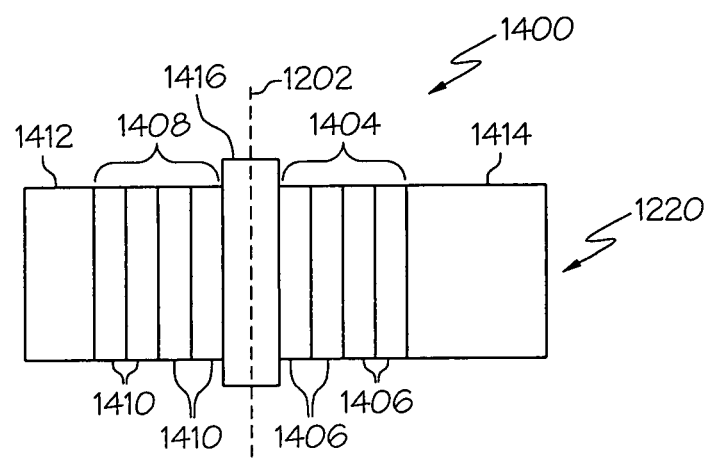
FIG. 14 illustrates one embodiment of an ultrasonic transducer having first and second piezoelectric stacks.

FIGS. 12-14 show embodiments of various transducers with a length less than one half (½) of one wavelength. Because of their small size, the embodiments shown in FIGS. 12-14 may be useful in smaller ultrasonic applications where lower ultrasonic power is required. In general, components in ultrasonic surgical instruments are dimensioned as integral multiples of half wavelengths ($n\lambda/2$). For example, transducers, waveguides and end effectors have a length that is usually an integral multiple of $\lambda/2$. Individual components, however, may have a length of less than $\lambda/2$, provided that the system as a whole (e.g., the transducer plus any end effector) has a length that is a multiple of $\lambda/2$. For example, a transducer, according to various embodiments, may have a length of between $\lambda/4$ and $\lambda/2$.

Figure 12A:
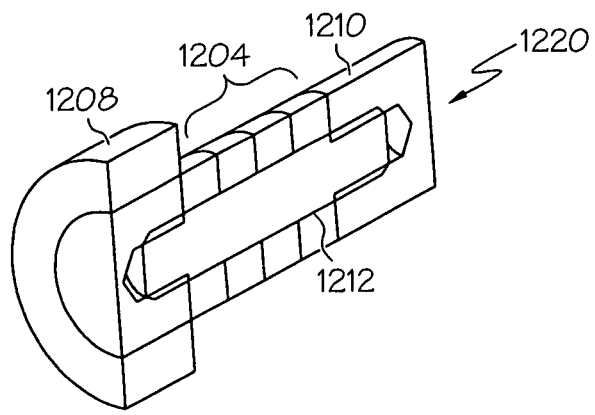
FIG. 12A illustrates a cut-away view of one embodiment of the quarter-wave ultrasonic transducer shown in FIG. 12.

FIG. 12 illustrates one embodiment of a quarter-wavelength ($\lambda/4$) ultrasonic transducer 1200. The transducer 1200 may include a flange 1208 and a mass 1210 with a piezoelectric stack 1204 positioned therebetween. The flange 1208 and mass may be made from any suitable material including, for example, metallic materials such as titanium or an alloy thereof. According to various embodiments, the flange 1208 may include an O-ring or other elastomeric material member (not shown) that may provide sealing as well as damping of vibrations within the flange 1208. The O-ring may be mounted within a groove or other feature of the flange (not shown), for example, as illustrated above in FIGS. 5-9. Also, according to various embodiments, the flange 1208 may be replaced with a second mass having radial dimensions similar to those of the piezoelectric stack 1204 and the mass 1210. FIG. 12A illustrates a cut-away view of one embodiment of the quarter-wave ultrasonic transducer 1200 illustrating a stud 1212. The stud 1212 may engage the elements 1206 of the piezoelectric stack 1204, placing them in compression. This may prevent the individual piezoelectric elements 1206 from being subjected to tension, which may cause mechanical failure.

In the embodiment shown in FIG. 12, a zero-displacement node 1202 of the transducer 1200 is indicated. The node 1202 may be located one quarter of one wavelength from the opposite edge 1220 of the transducer 1200. FIG. 13 illustrates one embodiment of an ultrasonic transducer 1300 that may be longer than a quarter wavelength. For example, the transducer 1300 may be dimensioned so that the node 1202 falls within flange 1208. In this way, the transducer stack 1204 may be closer to the node 1202. This may increase the effectiveness of the stack 1204. FIG. 14 illustrates one embodiment of an ultrasonic transducer 1400 having first and second piezoelectric stacks 1408 and 1404. The stacks 1404 and 1408 may be separated by a flange 1416, with masses 1412 and 1414 on the respective ends. According to various embodiments, the transducer 1400 may be between $\lambda/4$ and $\lambda/2$ in length.

FIGS. 15-19 illustrate embodiments of ultrasonic surgical devices having first and second operation members pivotable towards one another about a pivot point. A first operation member may comprise a transducer and an end effector coupled to the transducer. A second operation member may comprise a clamp pad. When the operation members are pivoted toward one another the clamp pad may be brought toward the end effector. The surgical instruments may be arranged according to any suitable configuration. For example, the embodiments shown in FIG. 15-17 may be arranged in a tweezer-like configuration. Also, for example, the embodiments shown in FIGS. 18-19 may be arranged with a scissor or pistol-like grip.

Figure 15:
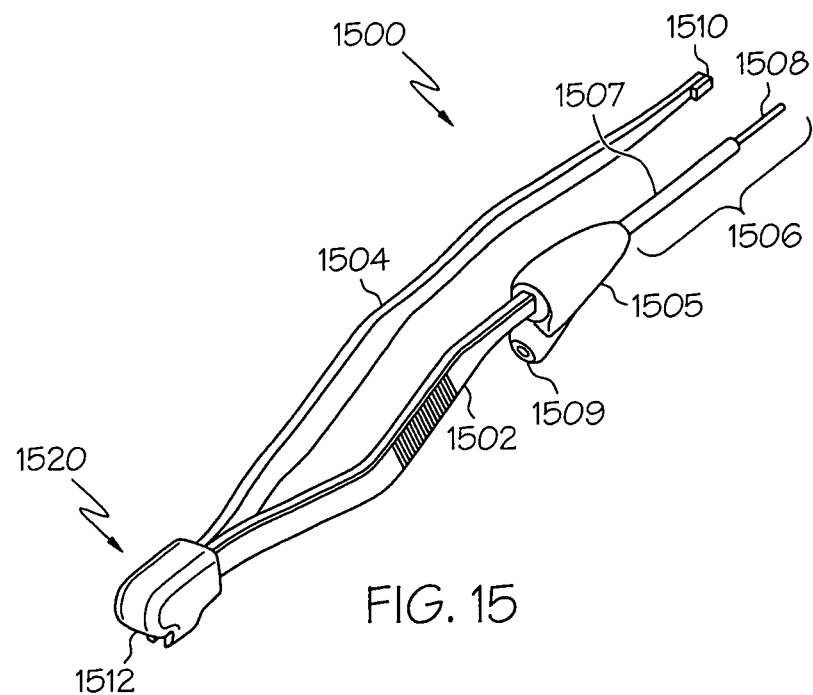
FIG. 15 illustrates one embodiment of an ultrasonic instrument.

FIG. 15 illustrates one embodiment of a surgical instrument 1500 having a first member 1504 and a second member 1502. The members 1502 may be pivotable toward one another about pivot point 1520. A support member 1512 may be positioned at the pivot point 1520 and may resist movements of the members 1504, 1502 toward or away from one another. According to various embodiments, the member 1502 may comprise a transducer assembly 1505 and an end effector 1506. The end effector 1506 may include a waveguide assembly 1507 and a blade 1508. A port 1509 may receive one or more wires (not shown) connecting the transducer assembly 1505 to a signal generator (not shown in FIG. 15). The end effector 1506 may comprise a waveguide and a protective sheath to prevent the waveguide from contacting tissue. The blade 1508 may operate as described above to cut and/or coagulate tissue. When the members 1504 and 1502 are pivoted together, the end effector 1508 may come into contact with the clamp pad 1510, allowing a clinician to apply pressure to tissue in contact with the blade 1508.

Figure 16:
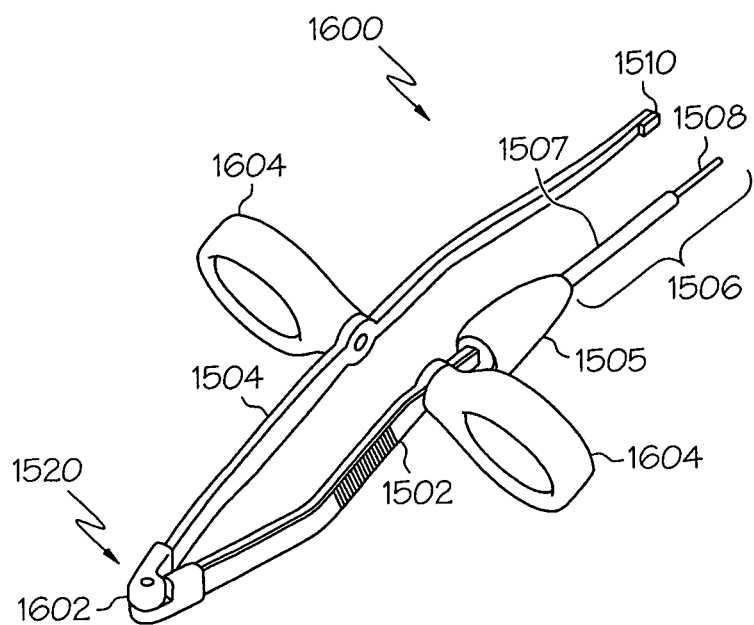
FIG. 16 illustrates one embodiment of an ultrasonic instrument having finger loops.
Figure 17:
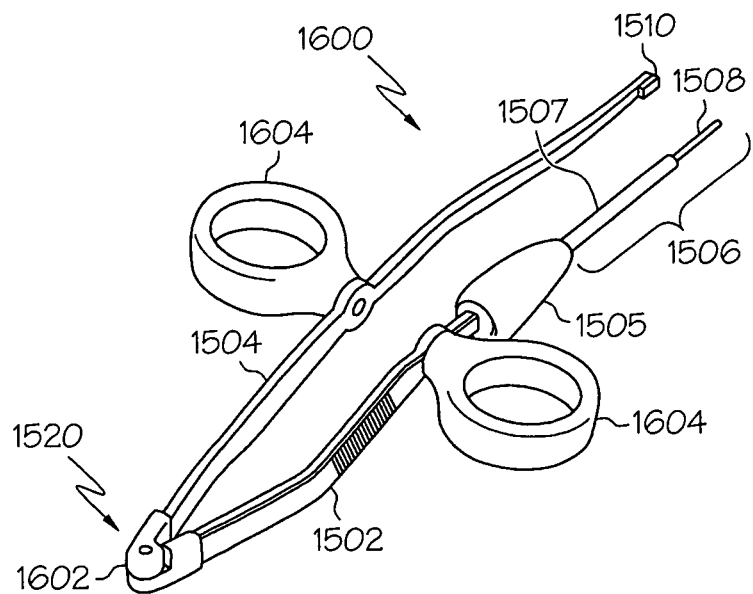
FIG. 17 illustrates one embodiment of the ultrasonic instrument shown in FIG. 16.

FIG. 16 illustrates one embodiment of an ultrasonic instrument 1600 similar to instrument 1500 and including finger loops 1604. The surgical instrument 1600 also may include a hinge 1602 at pivot point 1520. The hinge 1602 may allow the members 1502, 1504 to pivot freely about the pivot point 1520. The finger loops 1604 may be positioned on the members 1502, 1504 distally from the pivot point 1520. A clinician may use the finger loops 1604 to manipulate the members 1502, 1504. Also, according to various embodiments, the finger loops 1604 may be rotatable relative to the members 1502, 1504. For example, FIG. 17 illustrates one embodiment of the instrument 1600 with the finger loops 1604 rotated 90° relative to their position as shown in the embodiment of FIG. 16. It will be appreciated that the finger loops 1604 may be provided with holes large enough to fit multiple fingers.

Figure 18:
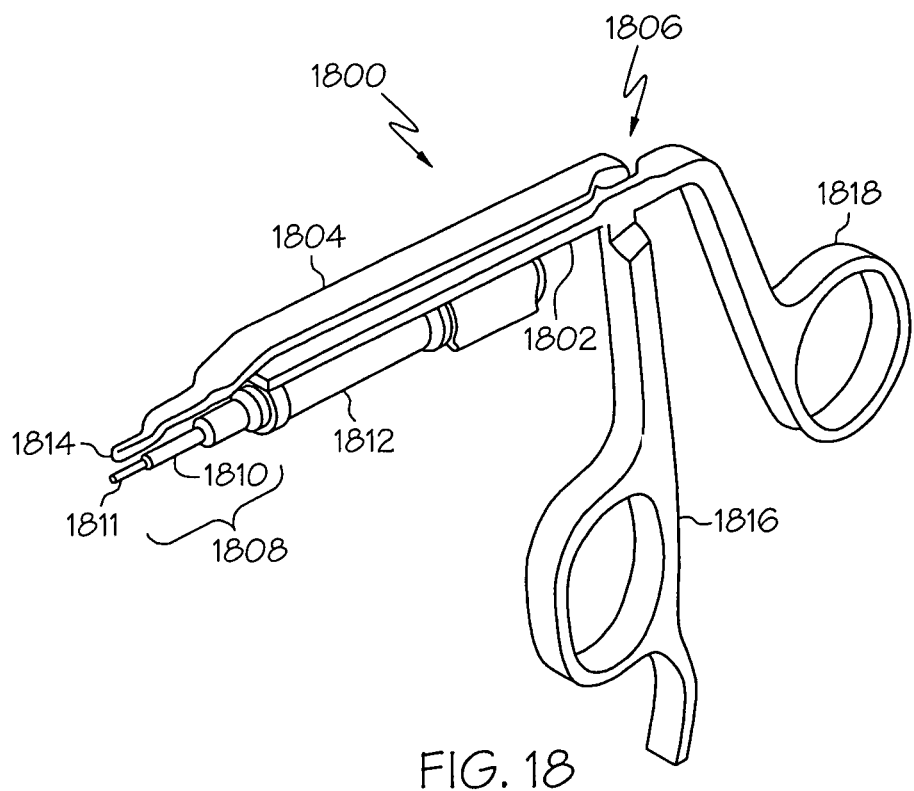
FIG. 18 illustrates one embodiment of an ultrasonic instrument.
Figure 19:
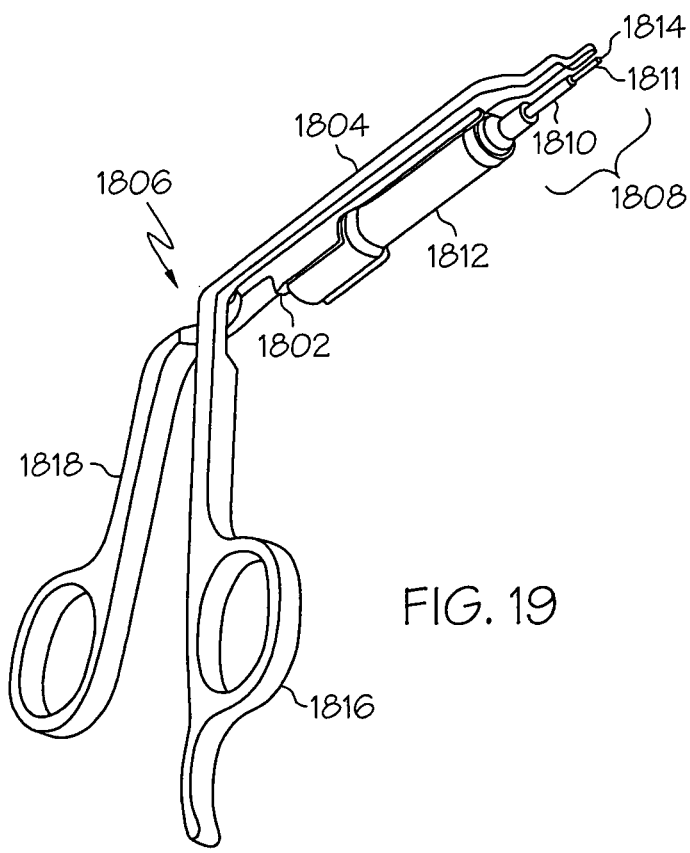
FIG. 19 illustrates one embodiment of the ultrasonic instrument shown in FIG. 18.

FIGS. 18-19 illustrate one embodiment of an ultrasonic instrument 1800. The instrument 1800 includes a first member 1802 and a second member 1804 pivotable towards one another about pivot point 1806. The first member 1802 may comprise a transducer assembly 1812 and an end effector 1808. The end effector 1808 includes a waveguide assembly 1810 and a blade 1811. The second member 1804 may comprise a clamp pad 1814 opposite blade 1811. When the members 1802, 1804 are pivoted towards one another, the clamp pad 1814 may come into contact with the blade 1811. In this way, a clinician may exert pressure on tissue in contact with the end effector 1808. Finger loops 1816 and 1818 may be positioned relative to the pivot point 1806 to allow a clinician to pivot the members 1802 and 1804 about the pivot point 1806 in a scissor-like manner. The finger loops 1816 and 1818 may be optionally angled, as shown, to create a "pistol-grip" configuration. It will be appreciated that the finger loops 1818 and 1816 may be provided with holes large enough to fit multiple fingers.

Figure 20:
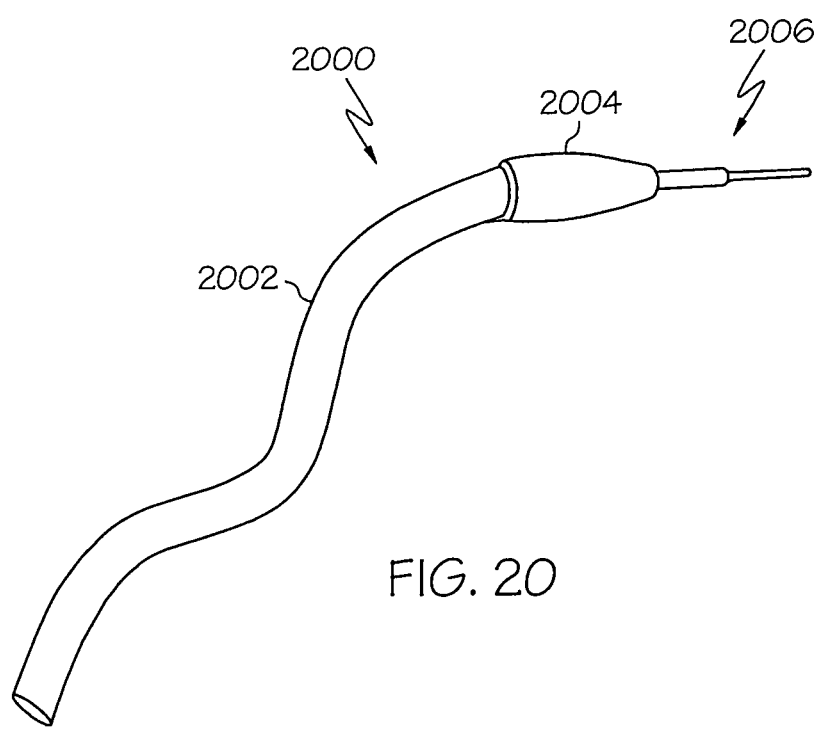
FIG. 20 illustrates one embodiment of an ultrasonic end effector and transducer assembly positioned at the distal end of a flexible member.

FIG. 20 illustrates one embodiment of an ultrasonic end effector 2006 and transducer assembly 2004 positioned at the distal end of a flexible member 2002. In use, other components, such as a handle, may be connected to the portion 2000.

FIGS. 21-26 show various embodiments of a surgical instrument that may be used in endoscopic or laparoscopic environments. The surgical instrument may comprise a surgical device including a transducer and an end effector. The surgical instrument also may comprise a sleeve configured to receive the surgical device. The sleeve may include a rail positioned along its interior portion. The surgical device may comprise a feature for receiving the rail. In use, the surgical device may slide within the sleeve along the rail. This may allow the surgical device to be introduced and removed from a surgical site during endoscopic or laproscopic surgical procedures.

Figure 21:
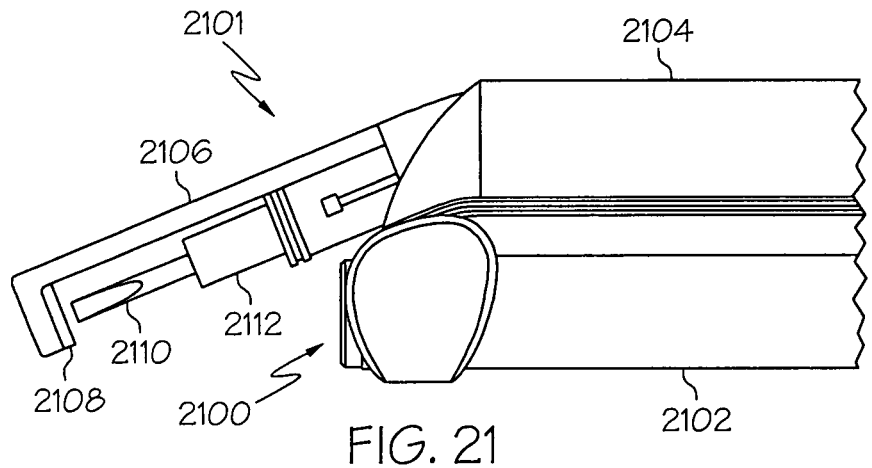
FIG. 21 illustrates one embodiment of an surgical instrument for use in an endoscopic or laparoscopic environment.

FIG. 21 illustrates one embodiment of an ultrasonic instrument 2101 for use in an endoscopic or laparoscopic environment. The surgical instrument 2101 may be housed within a sleeve 2104. The sleeve 2104 may be connected to an endoscope sleeve 2102 for housing the endoscope 2100. Portions of the surgical instrument 2101, e.g., a control wire, may extend through the sleeve 2104 to a clinician, who may control the surgical instrument 2101. The surgical instrument 2101 may be slidable within the sleeve 2104 into a position in view of the endoscope 2100, as shown.

Figure 22:
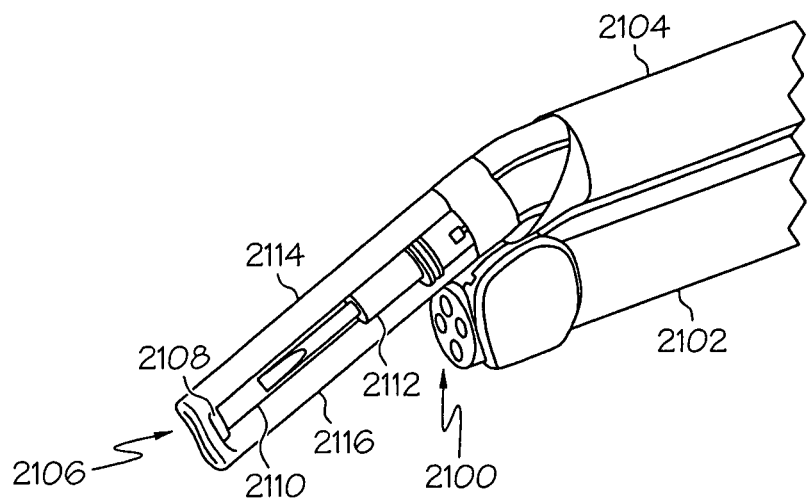
FIG. 22 illustrates one embodiment of the surgical instrument shown in FIG. 21.
Figure 23:
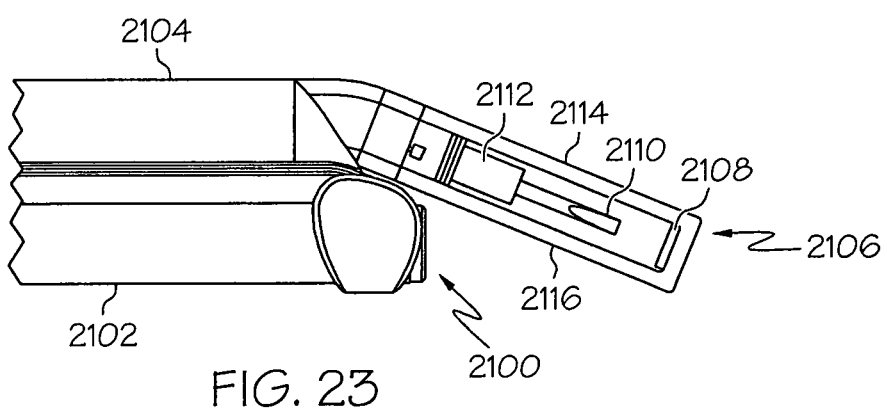
FIG. 23 illustrates one embodiment of the surgical instrument shown in FIG. 21.

The surgical instrument 2101 may comprise a transducer 2112, an end effector 2110, and a clamp arm 2106. The clamp arm 2106 may include a clamp pad 2108. In use, the clamp pad 2108 may be brought into contact with the end effector 2110 to provide a clamping force between tissue and the end effector 2110. For example, the surgical instrument may be maneuvered into position relative to the tissue. The end effector 2110 then may be energized and brought into contact with the tissue. According to various embodiments, the end effector 2110 may move toward the clamp arm 2106, or the clamp arm 2106 may move toward the end effector 2110. FIGS. 22-23 shows embodiments of the surgical instrument 2101 where the clamp arm 2106 comprises two support members 2114, 2116. The embodiments of FIGS. 22-23 may be utilized by drawing a loop or wedge of tissue between the two support members.

Figure 24:
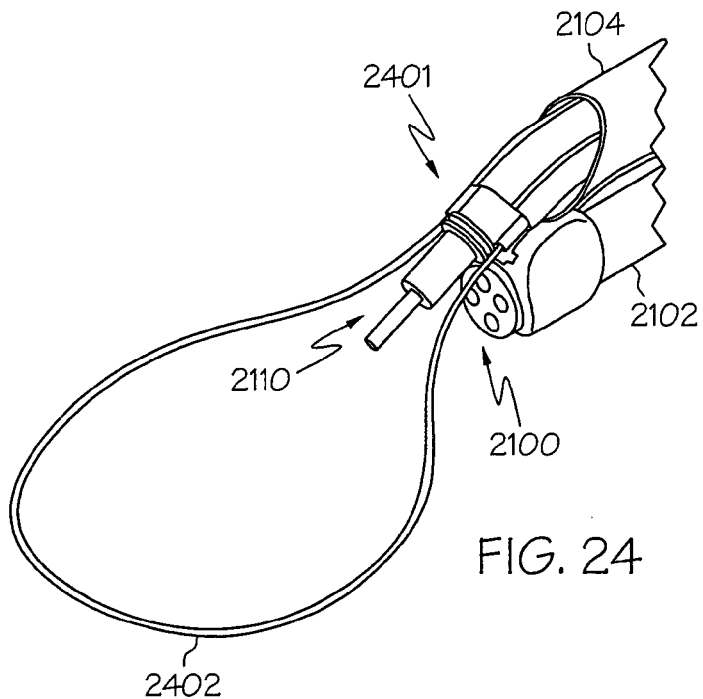
FIG. 24 illustrates one embodiment of the surgical instrument shown in FIG. 21 including a flexible lasso.
Figure 25:
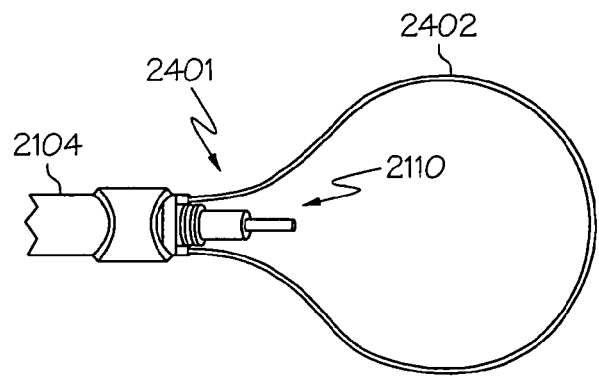
FIG. 25 illustrates one embodiment of the surgical instrument shown in FIG. 24.
Figure 26:
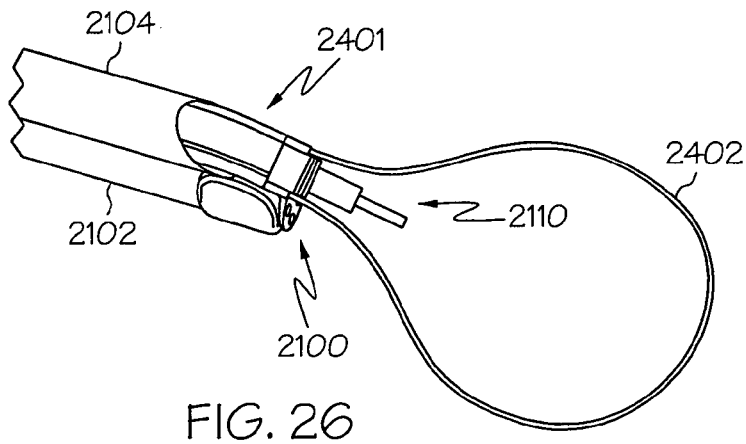
FIG. 26 illustrates one embodiment of the surgical instrument shown in FIG. 24.

FIGS. 24-26 illustrate embodiments of a surgical instrument 2401 including a flexible lasso 2402. The lasso 2402 may be extendable and retractable from the surgical instrument 2401 to bring tissue into contact with the end effector 2110. For example, a clinician may extend the lasso 2402 to ensnare a polyp or other type of tissue. The clinician then may retract the lasso 2402 to pull the polyp or other tissue into contact with the end effector 2110, which may be energized to cut and/or coagulate the tissue. The lasso 2402 may be embodied as a cable, or as a stiff ribbon material. It will be appreciated that a lasso 2402 made of stiff ribbon material may help guide tissue to the tip of the end effector 2110.

The instruments disclosed herein can be designed to be disposed of after a single use, or they can be designed to be used multiple times. In either case, however, the instrument may be reconditioned for reuse after at least one use. Reconditioning can include any combination of the steps of disassembly of the instrument, followed by cleaning or replacement of particular elements, and subsequent reassembly. In particular, the instrument may be disassembled, and any number of particular elements or components of the instrument may be selectively replaced or removed in any combination. Upon cleaning and/or replacement of particular components, the instrument may be reassembled for subsequent use either at a reconditioning facility, or by a surgical team immediately prior to a surgical procedure. Those skilled in the art will appreciate that reconditioning of a instrument may utilize a variety of techniques for disassembly, cleaning/replacement, and reassembly. Use of such techniques, and the resulting reconditioned instrument, are all within the scope of the present application.

Preferably, the various embodiments described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that the instrument is sterilized. This can be done by any number of ways known to those skilled in the art including beta or gamma radiation, ethylene oxide, steam.

Although various embodiments have been described herein, many modifications and variations to those embodiments may be implemented. For example, different types of end effectors may be employed. Also, where materials are disclosed for certain components, other materials may be used. The foregoing description and following claims are intended to cover all such modification and variations.

Other than the operating examples, or where otherwise indicated, all numbers expressing quantities of ingredients, processing conditions and the like used in the specification and claims are to be understood as being modified in all instances by the term "about". Accordingly, unless indicated to the contrary, the numerical parameters set forth in the following specification and attached claims are approximations that may vary depending upon the desired properties sought to be obtained.

Notwithstanding that the numerical ranges and parameters setting forth the broad scope of the disclosure are approximations, the numerical values set forth in the specific examples are reported as precisely as possible. Any numerical values, however, inherently contain certain errors, such as, for example, equipment and/or operator error, necessarily resulting from the standard deviation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of less than or equal to 10.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument, comprising:
a transducer configured to provide vibrations along a longitudinal axis at a predetermined frequency, the transducer comprising:
a piezoelectric stack positioned along the longitudinal axis;
a first metallic end mass positioned along the longitudinal axis adjacent a first end of the piezoelectric stack;
a second metallic end mass positioned along the longitudinal axis adjacent a second end of the piezoelectric stack, wherein the length of the transducer is greater than or equal to $1/4$ of one wavelength and less than $1/2$ of one wavelength; and
an end effector extending along the longitudinal axis coupled to the transducer at a location offset from a nearest anti-node, wherein a length of the end effector is a non-integer multiple of $1/2$ of one wavelength, and wherein a sum of the length of the transducer and the length of the end effector is an integer multiple of $1/2$ of one wavelength.

2. The surgical instrument of claim 1, wherein the end effector comprises a waveguide.

3. The surgical instrument of claim 1, wherein the piezoelectric stack comprises a plurality of piezoelectric elements.

4. The surgical instrument of claim 1, wherein the piezoelectric stack is positioned about at a node of the transducer, wherein the node is a point along the longitudinal axis about $1/4$ of one wavelength from an end of the transducer.

5. The surgical instrument of claim 1, wherein the length of the instrument is about one wavelength.

6. A method for processing a surgical instrument for surgery, comprising:
obtaining the surgical instrument of claim 1;
sterilizing the surgical instrument; and
storing the surgical instrument in a sterile container.

7. The surgical instrument of claim 1, wherein the sum, of the length of the transducer and the length of the end effector is about equal to ½ of one wavelength.

8. A surgical instrument, comprising:
- a transducer configured to provide vibrations along a longitudinal axis at a predetermined frequency, the transducer comprising:
  - a piezoelectric stack positioned along the longitudinal axis;
  - a first metallic end mass positioned along the longitudinal axis adjacent a first end of the piezoelectric stack;
  - a second metallic end mass positioned along the longitudinal axis adjacent a second end of the piezoelectric stack, wherein the amplitude gain of the transducer is equal to one; and
- an end effector extending along the longitudinal axis coupled to the transducer, wherein the end effector comprises:
  - a plurality of first sections positioned along the longitudinal axis having a first diameter;
  - a plurality of second sections positioned along the longitudinal axis between the plurality of first sections, wherein the plurality of second sections have a second diameter larger than the first diameter, wherein at least a portion of distally facing ends of the plurality of second sections are located at a first plurality of zero-displacement nodes, wherein at least a portion of proximally facing ends of the second sections are located at a second plurality of zero-displacement nodes, and wherein the first plurality and the second plurality of zero-displacement nodes do not include any zero-displacement nodes in common.

9. The surgical instrument of claim 8, wherein the end effector comprises a waveguide.

10. The surgical instrument of claim 8, wherein the amplitude gain of the ultrasonic surgical instrument is between about 10 and about 50.

11. A method for processing a surgical instrument for surgery, comprising:
- obtaining the surgical instrument of claim 8;
- sterilizing the surgical instrument; and
- storing the surgical instrument in a sterile container.

* * * * *